United States Patent [19]
Thompson et al.

[11] Patent Number: 6,130,053
[45] Date of Patent: *Oct. 10, 2000

[54] METHOD FOR SELECTING COMPOUNDS FOR INHIBITION OF NEOPLASTIC LESIONS

[75] Inventors: W. Joseph Thompson, Doylestown; Li Liu, Ambler; Han Li, Yardley, all of Pa.

[73] Assignee: Cell Pathways, Inc., Horsham, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 09/366,003

[22] Filed: Aug. 3, 1999

[51] Int. Cl.$^7$ .................................................. C12Q 1/48

[52] U.S. Cl. ............................................ 435/15; 435/69.2

[58] Field of Search .............................. 435/15, 69.2, 219

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,837,239 | 6/1989 | Benjamin et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |

(List continued on next page.)

FOREIGN PATENT DOCUMENTS

| | | |
|---|---|---|
| 0 330 004 A1 | 6/1989 | European Pat. Off. . |
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 743304 A1 | 5/1996 | European Pat. Off. . |
| 0 722 937 A1 | 7/1996 | European Pat. Off. . |
| 3038166 | of 1981 | Germany . |
| 274218 | 12/1989 | Germany . |
| 56-53659 | 5/1981 | Japan . |
| 57-167974 | 10/1982 | Japan . |

(List continued on next page.)

OTHER PUBLICATIONS

Waddell, W.R. et al., Am. J. Surgery, vol. 157, pp. 175–179 (1989).

Gilman, S.C. et al., Nonsteroidal Anti–inflammatory Drugs in Cancer Therapy, (circa 1985).

Duggan, D.E. et al., Clin. Pharm. & Therapeutics, vol. 21, No. 3, pp. 326–335 (1976).

Moorghen, M. et al., Journal of Pathology, vol. 156, pp. 341–347 (1988).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954,(Jun., 1980).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

(List continued on next page.)

*Primary Examiner*—Ralph Gitomer
*Attorney, Agent, or Firm*—Robert W. Stevenson

[57] ABSTRACT

A method for selecting compounds for the treatment of neoplasia includes assessing whether the compounds cause an increase in PKG activity in the neoplasia of interest.

12 Claims, 17 Drawing Sheets

U.S. PATENT DOCUMENTS

| | | |
|---|---|---|
| 5,223,501 | 6/1993 | Chakravarty et al. . |
| 5,239,083 | 8/1993 | Kumazawa et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,401,774 | 3/1995 | Pamukcu et al. . |
| 5,439,895 | 8/1995 | Lee et al. . |
| 5,464,861 | 11/1995 | Dobrusin et al. . |
| 5,488,055 | 1/1996 | Tulshian et al. . |
| 5,614,530 | 3/1997 | Kumar et al. . |
| 5,614,627 | 3/1997 | Takase et al. . |
| 5,674,876 | 10/1997 | Gilbert et al. . |
| 5,696,159 | 12/1997 | Gross et al. . |
| 5,728,563 | 3/1998 | Toshio et al. . |
| 5,731,167 | 3/1998 | Stracke et al. . |
| 5,756,818 | 5/1998 | Buchmann et al. . |
| 5,798,246 | 8/1998 | Au-Young et al. . |
| 5,798,373 | 8/1998 | Warrellow . |
| 5,824,305 | 10/1998 | Mynott ................................ 424/94.65 |
| 5,846,778 | 12/1998 | Hawkins et al. ....................... 435/69.1 |
| 5,849,770 | 12/1998 | Head et al. . |
| 5,852,035 | 12/1998 | Pamukcu et al. . |
| 5,858,694 | 1/1999 | Piazza et al. ............................. 435/19 |
| 5,869,519 | 9/1999 | Karanewsky et al. . |
| 5,874,440 | 2/1999 | Pamukcu et al. . |
| 5,891,896 | 4/1999 | Warrellow et al. . |
| 5,922,595 | 7/1999 | Fisher et al. . |
| 5,932,423 | 8/1999 | Au-Young et al. . |
| 5,932,465 | 8/1999 | Loughney . |
| 5,942,520 | 8/1999 | Pamukcu et al. . |
| 5,948,779 | 9/1999 | Sperl et al. . |

FOREIGN PATENT DOCUMENTS

| | | |
|---|---|---|
| 8-311035 | 11/1996 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 94/19351 | 9/1994 | WIPO . |
| WO 94/29277 | 12/1994 | WIPO . |
| WO 95 18969 | 7/1995 | WIPO . |
| WO 95/26743 | 10/1995 | WIPO . |
| WO 97/03070 | 1/1997 | WIPO . |
| WO 97/03985 | 2/1997 | WIPO . |
| WO 97/24334 | 7/1997 | WIPO . |
| WO 98/14448 | 4/1998 | WIPO . |
| WO 98/15530 | 4/1998 | WIPO . |
| WO 98/16224 | 4/1998 | WIPO . |
| WO 98/16521 | 4/1998 | WIPO . |
| WO 98/17668 | 4/1998 | WIPO . |
| WO 98/08848 | 5/1998 | WIPO . |
| WO 98/23597 | 6/1998 | WIPO . |
| WO 98/38168 | 9/1998 | WIPO . |
| WO 96/32379 | 10/1998 | WIPO . |
| WO 99/09199 | 2/1999 | WIPO . |
| WO 99/34018 | 7/1999 | WIPO . |
| WO 99/35283 | 7/1999 | WIPO . |
| WO 99/42481 | 8/1999 | WIPO . |

OTHER PUBLICATIONS

Chang, W. et al., Sulindac Sulfone Modulates the Expression and Cellular Localization of b–Catenin in Human Colon Carcinoma Cells, Digestive Disease Week, Apr. 1, 1999.

Peifer, M., β–Catenin as Oncogene: The Smoking Gun, Science, vol. 275, pp. 1752–1753, Mar. 21, 1997.

Korinek, V. et al., Constitutive Transcriptional Activation by a β–Catenin–Tcf Complex in $APC^{-/-}$ Colon Carcinoma, Science, vol. 275, pp. 1784–1786, Mar. 21, 1997.

Morin, P. et al., Activation of β–Catenin–Tcf Signaling in Colon Cancer by Mutations in β–Catenin or APC, Science, vol. 275, pp. 1787–1789, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Mahmoud, N. et al., Apc Gene Mutation is Associated with a Dominant–Negative Effect upon Intestinal Cell Migration, Cancer Research 57, pp. 5045–5050, Nov. 15, 1997.

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Earnest, D. et al., Piroxicam and Other Cyclooxygenase Inhibitors: Potential for Cancer Chemoprevention, Journal of Cellular Biochemistry, Supplement 161:156–166 (1992).

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Ahlstrom, M.; Lamberg–Allardt, C., Regulation of adenosine 3',5'–cyclic monophosphate (cAMP) accumulation in UMR–106 osteoblastlike cells: role of cAMP–phosphodiesterase and cAMP efflux, Biochem. Pharmacol. (1999), 58(8), 1335–1340.

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Ahn, Ho–Sam et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

Altiok N. et al., Bradykinin inhibition of cyclic AMP accumulation in D384 astrocytoma cells. Evidence against a role of cyclic GMP, Neurochem Int. Sep. 1992; 21(2):209–13.

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Antonenko S.G. et al., [The role of the components of the cyclic nucleotide system in N–nitrosodiethylamine–induced hepatic carcinogenesis in rats] (Article in Russian), Eksp. Onkol. 1990;12(5):18–21.

Badreih, Y., et al., Chem. Ber., vol. 125, pp. 667–674 (1992).
Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).
Belousova, A. K. et al., Role of cyclic nucleotides in tumor growth regulation, (Article written in Russian) Vestn. Akad. Med, Nauk SSSR (1980), (6), 86–9.
Beltman, Jerlyn et al., Characterization of cyclic nucleotide phosphodiesterases with cyclic GMP analogs: topology of the catalytic domains, Mol. Pharmacol. (1995), 47(2), 330–9.
Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).
Biddle, William et al., Antineoplastic Effect of the Pyrimido–Pyrimidine Derivative: RA 233, Pathologie Biologie, Jan., 1984, pp. 9–13.
Bjarnason et al., Gastroenterology, vol. 94, No. 4, pp. 1070–1074 (1988).
Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).
Brogden, R.N. et al., Drugs, vol. 16, pp. 97–114 (1978).
Broughton, B.J. et al., Antiallergic Activity of 2–Phenyl–8–azapruin–6–ones, Journal of Medicinal Chemistry, vol. 18, No. 11, pp. 1117–1118 (1975).
Butt, Elke et al., Characterization of cyclic nucleotide phosphodiesterases with cyclic AMP analogs: topology of the catalytic sites and comparison with other cyclic AMP–binding proteins, Mol. Pharmacol. (1995), 47(2), 340–7.
Carter et al., Chemotherapy of Cancer, $2^{nd}$ Ed., John Wiley & Sons, NY, NY, 1981, pp. 362–365.
Chang, W. et al., Sulindac Sulfone Modulates the Expression and Cellular Localization of b–Catenin in Human Colon Carcinoma Cells, Digestive Disease Week, Apr. 1, 1999.
Clarke, W. R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).
Cohan, V. L. et al., In vitro pharmacology of the novel phosphodiesterase type 4 inhibitor, CP–80633, J. Pharmacol. Exp. Ther. (1996), 278(3), 1356–1361.
Cohen L.A. et al., Cyclic nucleotide phosphodiesterase activity in normal and neoplastic rat mammary cells grown in monolayer culture, Cancer Res. Jun. 1976;36(6):2007–12.
Cote, Mylene, et al., Comparative involvement of cyclic nucleotide phosphodiesterases and adenylyl cyclase on adrenocorticotropin–induced increase of cyclic adenosine monophosphate in rat and human glomerulosa cells, Endocrinology (1999), 140(8), 3594–3601.
Curtis–Prior, P.B. et al., Cyclic Nucleotide Phosphodiesterase Activity of Human Normal and Carcinomatous Lung Tissue, The Lancet, pp. 1224–1225 Dec. 4, 1976.
Delporte C. et al., Role of phosphodiesterase II in cross talk between cGMP and cAMP in human neuroblastoma NB–OK–1 cells, Am. J. Physiol. Jan. 1996; 270(1 Pt 1):C286–92.

Dickinson, Natalie T. et al., Activation of cGMP–stimulated phosphodiesterase by nitroprusside limits cAMP accumulation in human platelets: effects on platelet aggregation, Biochem. J. (1997), 323(2), 371–377.
Drees, Markus et al., 3'5'–Cyclic Nucleotide Phosphodiesterase in Tumor Cells as Potential Target for Tumor Growth Inhibition, Cancer Researtch 53, pp. 3058–3061 (1993).
Duarte, Juan et al., Effects of visnagin on cyclic nucleotide phosphodiesterases and their role in its inhibitory effects on vascular smooth muscle contraction, Gen. Pharmacol. (1998), Volume Date 1999, 32(1), 71–74.
Duggan, D.E. et al., Clin. Pharm. & Therapeutics, vol. 21, No. 3, pp. 326–335 (1976).
Duggan, D.E. et al., J. Pharm. & Exper. Therap., vol. 201, No. 1, pp. 8–13 (1977).
Earnest, D. et al., Piroxicam and Other Cyclooxygenase Inhibitors: Potential for Cancer Chemoprevention, Journal of Cellular Biochemistry, Supplement 161:156–166 (1992).
Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.
Eckly–Michel, Anita E. et al., Chelerythrine, a protein kinase C inhibitor, interacts with cyclic nucleotide phosphodiesterases, Eur. J. Pharmacol. (1997), 324(1), 85–88.
Emami S. et al., Histamine and VIP interactions with receptor–cyclic AMP systems in the human gastric cancer cell line HGT–1, Life Sci. Aug. 1, 1983;33(5):415–23.
Epstein, P.M. et al. Increased Cyclic Nucleotide Phospho Di Esterase Activity Associated with Proliferation and Cancer in Human Murine Lymphoid Cells. Dep. Pharmacol., Univ. Tex. Med. Sch., M.D. Anderson Hospital, Houston, Tex. 77030, USA. BIOSIS: 78:140912 Abstract, No Date Given.
Federation Proceedings (1972) of the Federation of American Societies for Experimental Biology abstract Nos. 2044–2045.
Ferreira, S.H. et al., The molecular mechanism of action of peripheral morphone analgesia: stimulation of the cGMP system via nitric oxide release, European Journal of Pharmacology, 201 pp. 121–122 (1991).
Fischmeister, Rodolphe, et al., Cardiac calcium current regulation by the cGMP/NO pathway, C. R. Seances Soc. Biol. Ses Fil. (1996), 190(2–3), 181–206.
Folbergrova J. et al., Cyclic AMP levels of C6 glioma cells treated with cisdichlorodiammine platinum (cis–DDP), Neoplasma 1987;34(1):3–13.
Frattola L. et al., Characteristics of the cyclic AMP–phosphodiesterase activator in human brain tumours, J. Neurol. Sci. 1981 Nov.–Dec.;52(2–3):269–77.
Gaffen, J. D. et al.: Increased killing of malignant cells by giving indomethacin with methotrexate, p. 30; column 1; XP002084860Chemical Abstract, vol. 106, No. 11, Mar. 16, 1987, abstract No. 78377, J.D.
Gallo–Payet, Nicole et al., Cyclic AMP–independent effects of ACTH on glomerulosa cells of the rat adrenal cortex, J. Steroid Biochem. Mol. Biol. (1999), 69(1–6), 335–342.
Gilman, S.C. et al., Nonsteroidal Anti–inflammatory Drugs in Cancer Therapy, (circa 1985).
Giorgi M. et al., Induction of cyclic AMP and cyclic GMP 3':5'–cyclic nucleotide phosphodiesterase activities in nueroblastoma lines under differentiating conditions, Int. J. Dev. Neurosci. Jun. 1997;15(3):309–19.

Giorgi, Mauro et al., Characterization of 3':5' cyclic nucleotide phosphodiesterase activities of mouse neuroblastoma N18TG2 cells, FEBS Lett. 324(1) pp. 76–80 (1993).

Glavin, G.B. et al., Toxicology and Applied Pharmacology, vol. 83, pp. 386–389 (1986).

Gonzaga, R.A.F. et al., The Lancet, Mar. 30, 1985, p. 751.

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Haynes, Johnson, Jr. et al., Erythro–9–(2–hydroxy–3–nonyl) adenine inhibits cyclic–3',5'–guanosine monophosphate–stimulated phosphodiesterase to reverse hypoxic pulmonary vasoconstriction in the perfused rat lung, J. Pharmacol. Exp. Ther. (1996), 276(2), 752–7.

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Hucker, H.B. et al., Drug Metabolism & Disposition, vol. 1, No. 6, pp. 721–736 (1973).

Janik, P. et al., Inhibition of Growth of Primary and Metastic Lewis Lung Carcinoma Cells by the Phosphodiesterase Inhibitor Isobutylmethylxanthine, Cancer Res. vol. 40, pp. 1950–1954, (Jun., 1980).

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Kakkar R. et al., Calmodulin–dependent cyclic nucleotide phosphodiesterase (PDE1), Cell Mol. Life Sci. Jul. 1999;55(8–9):1164–86.

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Korinek, V. et al., Constitutive Transciptional Activation by a β–Catenin–Tcf Complex in APC$^{-/-}$Colon Carcinoma, Science, vol. 275, pp. 1784–1786, Mar. 21, 1997.

Kozai, Shigetada et al., Synthesis and biological activity of 9–(2,6–difluorobenzyl)–9H–purines bearing chlorine, Chem. Pharm. Bull. (1999), 47(4), 574–575.

Laasberg T. et al., Nerve growth factor increases the cyclic GMP level and activates the cyclic GMP phosphodiesterase in PC12 cells, FEBS Lett. Nov. 7 1988;239(2):367–70.

Law P.Y. et al., delta–Opioid receptor activates cAMP phosphodiesterase activities in neuroblastoma x glioma NG108–15 hybrid cells, Mol. Pharmacol. May 1993;43(5):684–93.

Leach M.O. et al., Measurements of human breast cancer using magnetic resonance spectroscopy: a review of clinical measurements and a report of localized 31P measurements of response to treatment, NMR Biomed. Nov. 1998;11(7):314–40.

Lichtner R. et al., Antimetastatic action of RX–RA 69, a new potent PDE–inhibitor in the Lewis lung carcinoma of the mouse, Prog. Clin. Biol. Res. 1982;89:131–41.

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Lichtner, Rosemarie B. et al., The pyrimidopyrimidine derivatives RA233 and RX–RA85 affect cell cycle distribution of two murine tumor cell lines, Eur. J. Cancer Clin. Oncol. 25(6) pp. 945–951 (1989).

Liu, Leo X. et al., Formation of cyclooxygenase–derived eicosanoids by a parasitic intravascular nematode, Adv. Prostaglandin, Thromboxane, Leukotriene Res. (1990), 21B (Prostaglandins Relat. Compd.), 509–12.

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Makaryan, A.P. et al., Cyclic Nucleotides in Patients with Malignant Neoplasms of the Colon, Laboratornoe Delo, vol. 8, pp. 31–33 (1991).

Mamytbekova, A. et al., Antimetastatic effect of flurbiprofen and other platelet aggregation inhibitors (Abstract Only), Neoplasma 33(4), pp. 417–421 (1986).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Marko D. et al., Induction of apoptosis by an inhibitor of cAMP–specific PDE in malignant murine carcinoma cells overexpressing PDE activity in comparison to their nonmalignant counterparts, Cell Biochem Biophys. 1998;28(2–3):75–101.

Mehta, Rajendra et al., Structure–Activity Relationships of Brassinin in Preventing the Development of Carcinogen–Induced Mammary Lesions in Organ Culture, Anticancer Research 14: 1209–1214 (1994).

Mery, Pierre–Francois et al., EHNA as an inhibitor of PDE2: A pharmacological and biochemical study in cardiac myocytes, Phosphodiesterase Inhib. (1996), 81–88.

Michie, Alison M. et al., Rapid regulation of PDE–2 and PDE–4 cyclic AMP phosphodiesterase activity following ligation of the T cell antigen receptor on thymocytes: analysis using the selective inhibitors erythro–9–(2–hydroxy–3–nonyl)–adenine (EHNA) and rolipram, Cell. Signalling (1996), 8(2), 97–110.

Mitchell, J.A. et al., Selectivity of nonsteroidal antiinflammatory drugs as inhibitors of constitutive and inducible cyclooxygenase; Proc. Natl. Acad. Sci. USA, vol. 90, Dec. 1994, pp 11693–11697.

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Moorghen, M. et al., Acta Histochemica, Suppl.–Band XXIX, S. 195–199 (1990).

Morgan A.J. et al., Comparison of the effect of isobutylmethylxanthine and phosphodiesterase–selective inhibitors on cAMP levels in SH–SY5Y neuroblastoma cells, Biochem. Pharmacol. Jun. 22, 1993;45(12):2373–80.

Morin, P. et al., Activation of β–Catenin–Tcf Signaling in Colon Cancer by Mutations in β–Catenin or APC, Science, vol. 275, pp. 1787–1789, Mar. 21, 1997.

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Nagai T. et al., Distinct isozyme patterns of cyclic nucleotide phosphodiesterase in human neuroblastoma and ganglioneuroma; a possible market of differentiation of neural crest-–derived tumors and Schwann cells, Jpn. J. Cancer Res. Jan. 1986; 77(1):52–8.

Nakai A. et al., High activity of cyclic 3',5'–nucleotide phosphodiesterase in sera of patient with phaeochromocytoma, Clin. Endocrinol. (Oxf) Apr. 1986;24(4):409–14.

Naskalski J.W. et al., Correlation of granulocyte intracellular activities of cyclic nucleotide phosphodiesterases with leukocyte count in patients with chronic myelogenous leukaemia, Haematologia (Budap) 1986;19(4):285–92.

Nichols M.R. et al., Tyrosine kinase–independent inhibition of cyclic–AMP phosphodiesterase by genistein and tyrphostin 51, Arch. Biochem. Biophys. Jun. 15 1999;366(2):224–30.

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

O'Donnell, James M. et al., Behavioral effects of family-–selective inhibitors of cyclic nucleotide phosphodiesterases, Pharmacol., Biochem. Behav. (1999), 63(1), 185–192.

Oldham S.B. et al., Presence of calmodulin in parathyroid adenomas, Miner Electrolyte Metab. 1982;7(5):273–80.

Patel, V. et al., Plasma cAMP and cAMP–phosphodiesterase (PDE) levels in cancer patients before and after surgery, Indian J. Cancer Sep. 1981;18(3):181–4.

Peifer, M., β–Catenin as Oncogene: The Smoking Gun, Science, vol. 275, pp. 1752–1753, Mar. 21, 1997.

Pepin, P. et al., Effects of Sulindac and Oltipraz on the tumorigenicity of 4–(methylnitrosamino)1–(3–pyridyl)–1–Butanone in A/J mouse lung, Carcinogenesis vol. 13 No. 3 pp. 341–348 (1992).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Radomski, Marek W., et al., Human Colorectal adenocarcinoma cells: differential nitric oxide synthesis determines their ability of aggregate platelets (Abstract Only), Cancer Res. 51(22) pp. 6073–6078 (1991).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Redmond O.M., Tissue characterization and assessment of preoperative chemotherapeutic response in musculoskeletal tumors by in vivo 31P magnetic resonance spectroscopy, Magn. Reson. Med. Oct. 1992;27(2):226–37.

Rivet–Bastide, Michele et al., cGMP–stimulated cyclic nucleotide phosphodiesterase regulates the Basal calcium current in human atrial myocytes, J. Clin. Invest. (1997), 99(11), 2710–2718.

Rosman, Guy J. et al., Isolation and characterization of human cDNAs encoding a cGMP–stimulated 3',5'–cyclic nucleotide phosphodiesterase, Gene (1997), 191(1), 89–95.

Rubinfeld, B. et al., Stabilization of β–Catenin by Genetic Defects in Melanoma Cell Lines, Science, vol. 275, pp. 1790–1792, Mar. 21, 1997.

Sadhu, Krishna et al., Differential expression of the cyclic GMP–stimulated phosphodiesterase PDE2A in human venous and capillary endothelial cells, J. Histochem. Cytochem. (1999), 47(7), 895–905.

Saeki, T. et al., Isolation of Cyclic Nucleotide Phosphodiesterase Isozymes From Pig Aorta, Biochem. Pharmacology, vol. 46, No. 5, pp. 833–839 (1993).

Savini F. et al., Phosphodiesterase in human colon carcinoma cell line CaCo–2 in culture, Life Sci. 1995;56(22):PL421–5.

Schudt, Christian et al., "Phosphodiesterase Inhibitors" The Handbook of Immunopharmacology, Academic Press, 1996, pp. 65–134.

Semmler, J. et al., Xanthine derivatives: comparison between suppression of tumor necrosis fator–x production and inhibition of cAMP phosphodiesterase activity, Immunology 78, pp. 520–525 (1993).

Shen, T.Y. et al., Chemical and Biological Studies on Indomethacin, Sulindac and Their Analogs, pp. 170–178 (circa 1975).

Sheth S.B. et al., Isolation and regulation of the cGMP–inhibited cAMP phosphodiesterase in human erythroleukemia cells, Thromb. Haemost Jan. 1997;77(1):155–62.

Silvola, J. et al., Effects of nonsteroidal anti–inflammatory drugs on rat gastric mucosal phosphodiesterase activity, Agents and Actions, vol. 12.4, pp. 516–520 (1982).

Singh R.P. et al., Plasma c–AMP and c–AMP–PDE activity in carcinoma of uterine cervix, Mater Med. Pol. Apr.–Jun. 1988;20(2):76–8.

Solntseva T.I. et al., [Some feature of cyclic adenosine monophosphate metabolism in mouse liver and hepatoma 22] (Article in Russian), Biokhimiia Jul. 1977; 42(7):1331–7.

Souness, John E. et al., Role of Selective cyclic GMP phosphodiesterase inhibition in the myorelaxant actions of M&B 22,943, MY–5445, vinpocetine and 1–methyl–3–isobulyl–8–(methylamino)xanthine (Abstract Only), Br. J. Pharmacol. 98(3) pp. 725–734 (1989).

Stevens R.H. et al., Adenosine 3',5'–cyclic monophosphate and guanosine 3',5'–cyclic monophosphate phosphodiesterase activities in 1,2–demethylhydrazine induced colon adenocarcinoma, Cancer Lett. Aug. 1979;7(4):227–34.

Stevens R.H. et al., Adenosine and guanosine 3',5' cyclic monophosphate phosphodiesterase activities in rat small and large bowel following single and multiple exposure to 1,2–demethylhydrazine, Drug Chem. Toxicol. 1981;4(2):161–72.

Torphy T.J. et al., Stimulation of beta adrenoceptors in a human monocyte cell line (U937) up–regulates cyclic AMP–specific phosphodiesterase activity, J. Pharmacol. Exp. Ther. Dec. 1992;263(3):1195–205.

Tsou, K–C. et al. 5'–Nucleotide Phosphodiesterase Isozyme–V as a Marker for Liver Metastases in Breast Cancer Patients, Cancer 54:1788–1793, 1984.

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Turnbull J.L. et al., The isolation and characterization of cyclic nucleotide phosphodiesterases from Morris hepatoma 5123tc(h) and rat liver, Int. J. Biochem. 184;16(1):19–29, No Date Given.

Turner, N.C. et al., Pulmonary effects of type V cyclic GMP specific phosphodiesterase inhibition in anaesthetized guinea–pig, Br. J. Pharmacol., vol. 111, 1198–1204 (1994).

Turner, N.C. et al., Relaxation of guinea–pig trachea by cyclic AMP phosphodiesterase inhibitors and their enhancement by sodium mitroprusside, Br. J. Pharmacol., vol. III, pp. 1047–1052 (1994).

Tzanakakis G.N. et al., Prevention of human pancreatic cancer cell–induced hepatic metastasis in nude mice by dipyridamole and its analog RA–233, Cancer Apr. 15, 1993;71(8):2466–71.

Van Lookeren Campagne, Michiel M. et al., Characterization of the yeast low Km cAMP–phosphodiesterase with cAMP analogs. Applications in mammalian cells that express the yeast PDE2 gene, J. Biol. Chem. (1990), 265(10), 5847–54.

Verde, Ignacio et al., Characterization of the cyclic nucleotide phosphodiesterase subtypes involved in the regulation of the L–type Ca2+ current in rat ventricular myocytes, Br. J. Pharmacol. (1999), 127(1), 65–74.

Waddell, W.R. et al., J. Surg. Oncology, vol. 24, pp. 83–87 (1983).

Weishaar, R.E. et al., A new generation of phosphodiesterase inhibitors: multiple molecular forms of phosphodiesterase and the potential for drug selectivity, J. Med. Chem. 185 May;28(5):537–45, No Date Given.

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Xin Y., [Relationship between cyclic nucleotide phosphodiesterases (cPDE) and some patho–biologic behaviors of stomach cancer—I. Histochemical studies of CPDE in stomach cancer tissues], (Article in Chinese), Chung Hua Chung Liu Tsa Chih Mar. 1989; 11(2):117–20.

Yamashita, Nobuyuki et al., Rolipram, a phosphodiesterase–4–selective inhibitor, promotes the survival of cultured rat dopaminergic neurons, Jpn. J. Pharmacol. (1997), 75(2), 155–159.

Yamashita, Nobuyuki et al., Rolipramm, a selective inhibitor of phosphodiesterase type 4, pronouncedly enhanced the forskolin–induced promotion of dopamine biosynthesis in primary cultured rat mesencephalic neurons, Jpn. J. Pharmacol. (1997), 75(1), 91–95.

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073–2081 (1992).

Zacharski, L. R. et al., Effect of Mopidamol on Survival in Carcinoma of the Lung and Colon: Final Report of Verterans Administration Cooperative Study No. 188, J. of the Nat'l. Cancer Inst. vol. 80, No. 2, pp. 90–96 (1988).

Zacher, L. A; Carey, G. B., Cyclic AMP metabolism by swine adipocyte microsomal and plasma membranes, Comp. Biochem. Physiol., Part B: Biochem. Mol. Biol. (1999), 124B(1), 61–71.

Zurbonsen K. et al., Dissociation between phosphodiesterase inhibition and antiproliferative effects of phosphodiesterase inhibitors on the Dami cell line, Biochem. Pharmacol. Apr. 25, 1997;53(8):1141–7.

Lim J. Sulindac Derivatives Inhibit Growth and Induce Apoptosis in Human Prostate Cancer Cell Lines. Biochemical Pharmacology vol. 58, pp. 1097–1107, 1999.

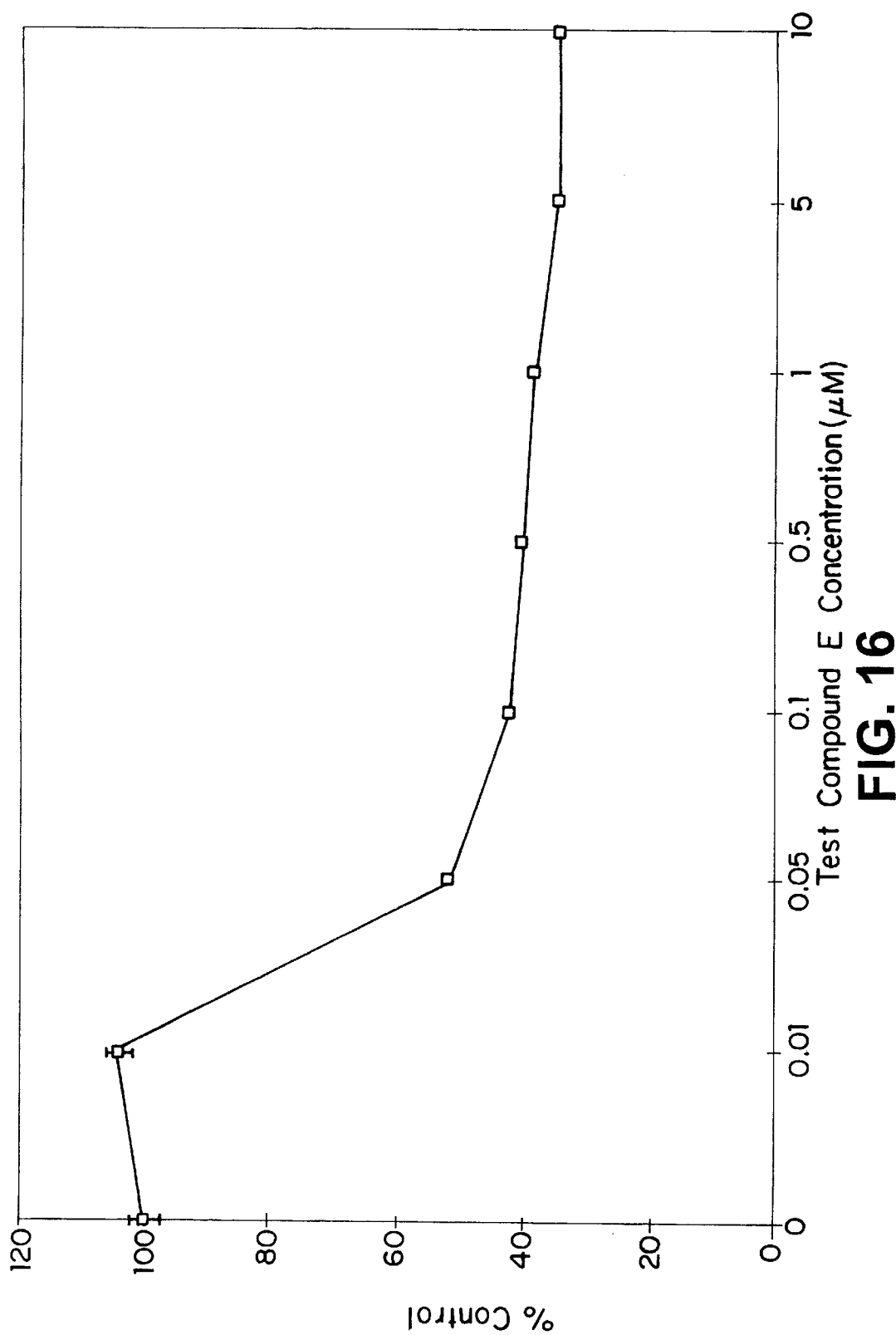

18A. in the absence of cGMP
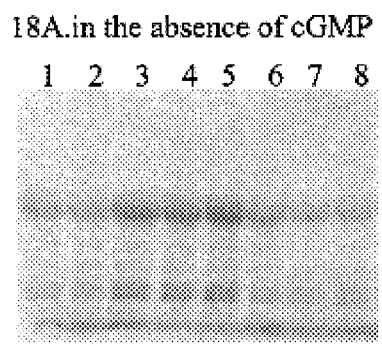
18B. in the presence of 8uM cGMP
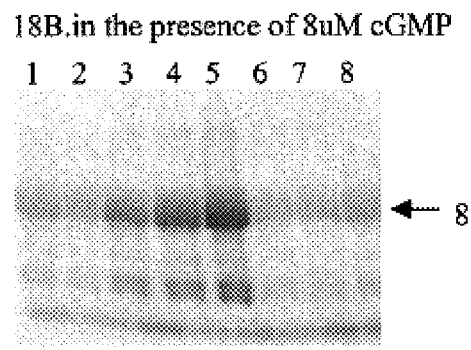
← 85Kd
Figure 18A          Figure 18B
Protein kinase G activity from drug-treated SW480 cell lysates.
SW480 cells were treated with DMSO (0.03%, lanes 1 and 2), Exisulind (200, 400 and 600μM; lanes 3, 4, 5, respectively) and E4021 (0.1, 1 and 10μM, lanes 6, 7, 8, respectively) for 48 hrs.

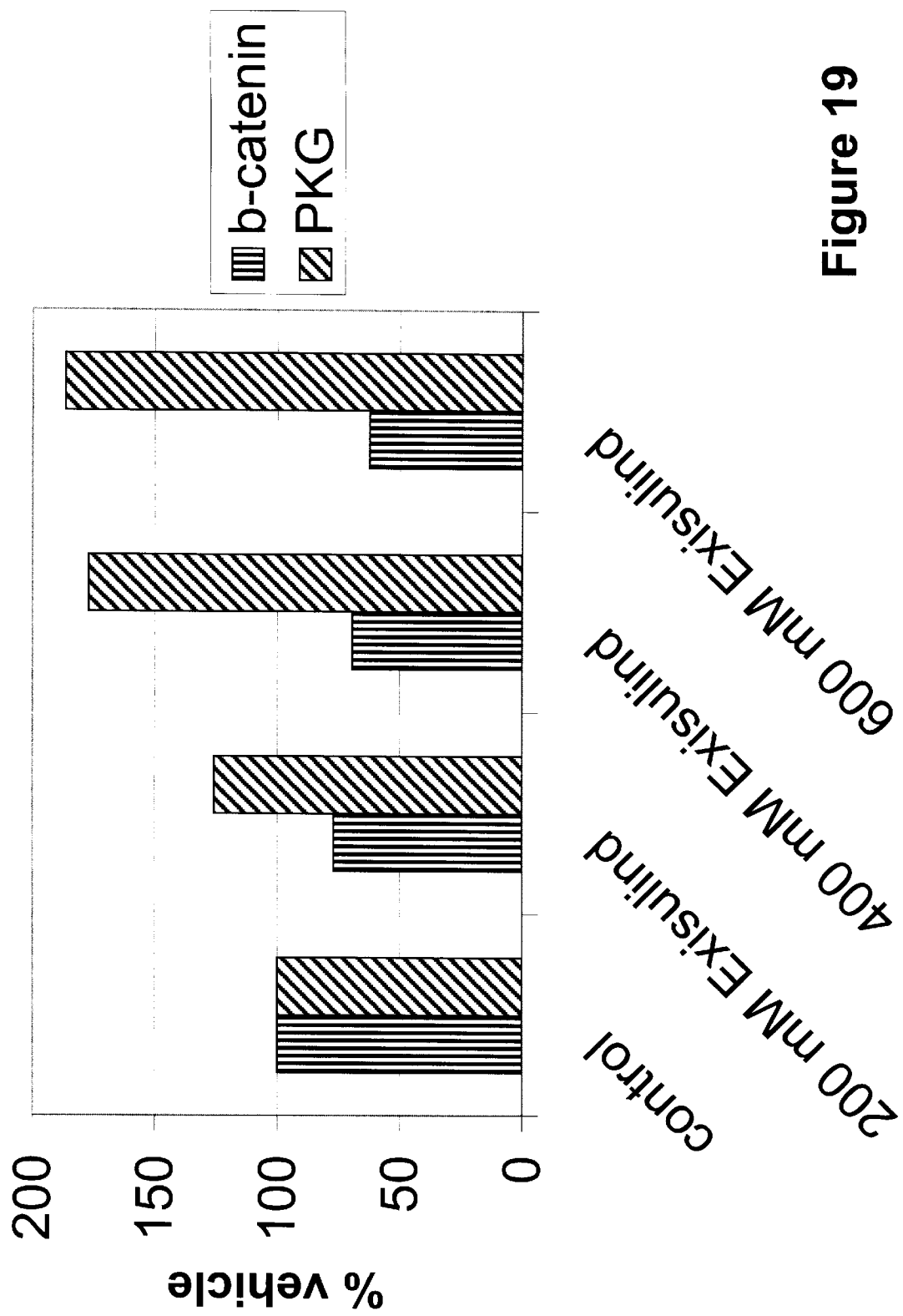

METHOD FOR SELECTING COMPOUNDS FOR INHIBITION OF NEOPLASTIC LESIONS

BACKGROUND OF THE INVENTION

This invention provides a method for selecting compounds potentially useful for the treatment and prevention of pre-cancerous and cancerous lesions in mammals.

For many years, researchers have sought compounds that selectively treat neoplastic cells without substantial growth-inhibiting adverse effects on normal cells. Conventional cancer chemotherapeutics—regardless of the type of cancer against which they have been directed—share one common feature: conventional compositions (e.g., herceptin, taxol, cisplatin, tamoxifen etc), to the extent they have any substantial effects on neoplastic cells—virtually always have significant adverse effects on normal tissues. Many of the side effects are debilitating and life-threatening. Thus, conventional chemotherapeutics are typically administered only after the neoplasia has significantly progressed to the stage where the drug side effects clearly outweigh the risks of no chemotherapy.

Conventional chemotherapeutics also typically are used to treat fairly specific types of neoplasias. For example, leuprolide is commonly prescribed to treat advanced prostate cancer, but not colon or lung cancers. Compositions with activities against broader ranges of neoplasias are desired.

Pamukcu et al., in U.S. Pat. No. 5,401,774, compounds such those now known as exisulind are disclosed for anti-neoplastic purposes. Contrary to conventional chemotherapeutics, such compounds are selective against neoplastic cells as opposed to normal cells. Thus, such compounds can be administered on a chronic basis without the side effects normally associated with conventional chemotherapeutics. In addition, because of their safety profile, such compounds can be administered at the earliest stages of disease. Thus, new compounds have become recognized as a new class of antineoplastics known as selective apoptotic anti-neoplastic drugs ("SAANDs").

Besides outstanding safety advantages over conventional chemotherapeutics, SAANDs also have a wider range of therapeutic application compared to conventional chemotherapeutics. For example, the first SAAND, exisulind, has been reported to have anti-neoplastic effects on colon, breast, lung, prostate, kidney, and melanoma neoplasias. It also has effects on other neoplasias.

SAANDs have the further advantage over anti-neoplastic NSAIDS (e.g., sulindac) because, unlike NSAIDs, SAANDs do not inhibit COXI or II enzymes. Inhibition of COX I and/or COX II enzymes (e.g., by indomethacin, celecoxib and other NSAIDs) lead to considerable side effects when taken on a chronic basis. In addition, COX inhibition is unnecessary for anti-neoplastic efficacy. Not surprisingly, not all COX I and COX II inhibitors (e.g., carprofen) also have been demonstrated to have significant anti-neoplastic activities. The side effects of COX I and COX II inhibitors include gastric irritations that can lead to severe ulceration, and kidney toxicities. Since SAANDs antineoplastic therapy is enhanced with chronic or long-term administration, the COX inhibitors—to the extent any exhibit anti-neoplastic properties—are inappropriate simply because of safety considerations, since few patients can realistically take COX inhibitors chronically or long-term. For inflammation, COX inhibitors are commonly used only on a short-term or acute basis as a result.

How SAANDs act without the side effects of COX inhibitors (or the even more severe side effects of conventional chemotherapeutics) remained a mystery until recently. As reported in U.S. Pat. No. 5,858,694, SAANDs work, in part by the inhibition of PDE5, which appears to be a necessary part of how SAANDs induce apoptosis (a form of cell death) in neoplastic, but not in normal cells. It was also discovered that SAANDs work by increasing cGMP and reducing cAMP in neoplastic cells, also as reported in the '694 patent.

However, it was later discovered that some PDE5 inhibitors did not singly (i.e. without other compounds) induce apoptosis (see, e.g. U.S. patent application Ser. No. 09/173,375 filed Oct. 15, 1998). In the '375 application, the discovery of a new cGMP-specific PDE found in neoplastic cells was first reported. One observation that separated anti-neoplastic PDE5 inhibitors from other PDE5 inhibitors was that the anti-neoplastic PDE5 inhibitors inhibited the new cGMP-specific PDE, whereas the other PDE5 inhibitors (e.g., sildenafil) had little relative effect. This observation, as disclosed in the '375 application, led to more accurate drug discovery screening methods to identify anti-neoplastic PDE5 inhibitors (i.e. additional SAANDs).

However, more accurate and alternative methods to evaluate and identify compounds for their usefulness as SAANDs are desired.

SUMMARY OF THE INVENTION

This invention relates to a novel method for screening and identifying compounds for their usefulness as SAANDs. In particular, this invention provides a method for identifying compounds that can be used to treat and prevent neoplasia, including precancerous lesions, with minimal side effects associated with COX inhibition and other non-specific interactions associated with conventional chemotherapeutics.

This invention has several embodiments. Those involve evaluating whether a compound causes an increase in cGMP-dependent protein kinase G ("PKG") activity and/or a decrease of β-catenin in neoplastic cells. It has been found that unexpected characteristics of SAANDs include the elevation of PKG activity and a decrease in β-catenin in neoplastic cells exposed to a SAAND. The other characteristics of SAANDs is (1) their inhibition of PDE5 as reported in the '694 patent above, (2) their inhibition of the novel cGMP-specific PDE described in the '375 application, (3) the fact that they cause cGMP to rise in neoplastic cells, and (4) the fact that they cause cAMP levels to fall.

Thus, one embodiment of the novel method of this invention is evaluating whether a compound causes PKG activity to elevate in neoplastic cells and whether that compound inhibits PDE5. Another embodiment of the novel screening method of this invention is evaluating whether a compound that causes PKG activity to elevate in neoplastic cells and whether that compound inhibits the novel cGMP-specific PDE described below and in the '375 application. Still a third embodiment is evaluating whether a compound causes PKG activity to elevate in neoplastic cells and whether that compound causes cGMP to rise in neoplastic cells and/or causes cAMP levels to fall. Compounds successfully evaluated in such fashions have application as SAANDs.

In still other embodiments of this invention, therefore, the screening method involves determining the COX inhibition activity of a test compound, low COX I and/or COX II inhibition being desired from an adverse events perspective. Preferably, the screening method of this invention further includes determining whether the compounds inhibit the growth of neoplastic cells, e.g., in a cell culture or in vivo. Preferably, the growth inhibition is achieved by inducing apoptosis.

By screening compounds in this fashion, potentially beneficial and improved SAANDs can be identified more rapidly and with greater precision than possible in the past. Further benefits will be apparent from the detailed description that follows.

BRIEF DESCRIPTION OF THE DRAWINGS

FIG. 16 illustrates the growth inhibitory activity of compound E.

FIG. 18A is a Western blot of SW480 cell lysates from drug-treated cell lysates in the absence of added cGMP, where cells were treated in culture for 48 hours with DMSO (0.03%, lanes 1 and 2), exsulind (200, 400 and 600 µM; lanes 3, 4, 5) and E402 1 (0.1, 1 and 10 µM , lanes 6, 7, 8).

FIG. 18B is a Western blot of SW480 cell lysates from drug-treated cell lysates in the presence of added cGMP, where cells were treated in culture for 48 hours with DMSO (0.03%, lanes 1 and 2), exsulind (200, 400 and 600 µM; lanes 3, 4, 5) and E4021 (0.1, 1 and 10 µM, lanes 6, 7, 8).

FIG. 19 is a bar graph of the results of Western blot experiments of the effects of exisulind on β-catenin and PKG levels in neoplastic cells relative to control.

DETAILED DESCRIPTION OF THE PREFERRED EMBODIMENTS

In General

Figure 1:
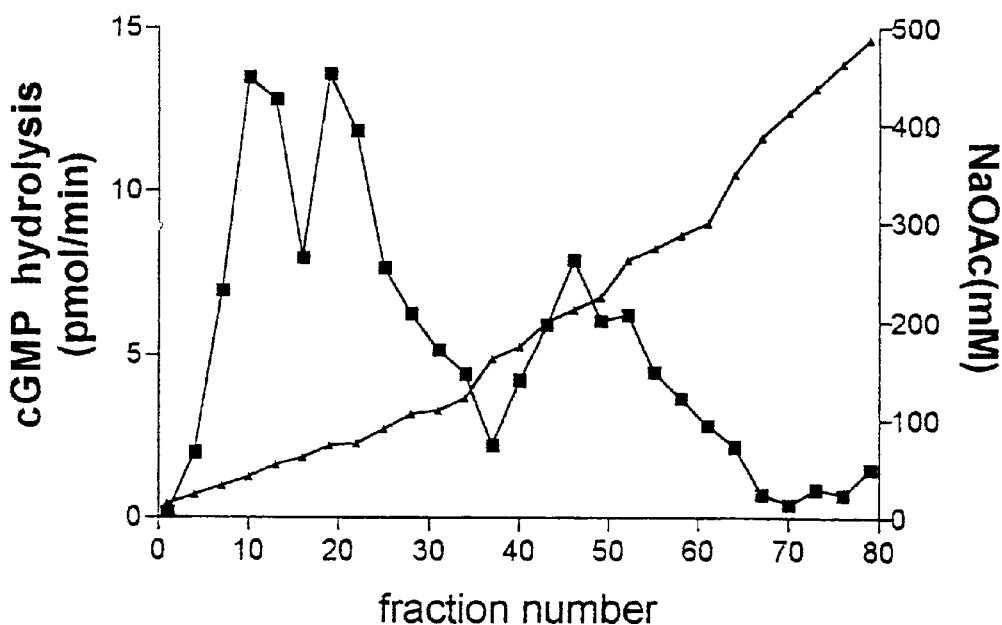
FIG. 1 is a graph of the cGMP activities of the cGMP phosphodiesterases obtained from SW480 neoplastic cells, as assayed from the eluent of a DEAE-Trisacryl M liquid chromatography column.

A series of experiments were performed to ascertain what effect, if any, an anti-neoplastic cGMP-specific PDE inhibitor had on cGMP-dependent protein kinase G ("PKG") in neoplastic cells containing either the adenomatous polyposis coli gene ("APC gene") defect or a defect in the gene coding for β-catenin. As explained below, such an inhibitor causes an elevation in PKG activity in such neoplastic cells. That increase in activity was not only due to increased activation of PKG in cells containing either defect, but also to increased expression of PKG in cells containing the APC defect. In addition, when PKG from neoplastic cells with either defect is immunoprecipitated, it precipitates with β-catenin.

β-catenin has been implicated in a variety of different cancers because researchers have found high levels of it in patients with neoplasias containing mutations in the APC tumor-suppressing gene. People with mutations in this gene at birth often develop thousands of small tumors in the lining of their colon. When it functions properly, the APC gene codes for a normal APC protein that is believed to bind to and destroy β-catenin. Thus, the discovery that PKG in neoplastic cells containing either the APC gene defect or the β-catenin defect is bound to β-catenin indeed strongly implicates PKG in one of the major cellular pathways that leads to cancer. In addition, because of the relationship between cGMP-specific inhibition and PKG elevation upon treatment with SAANDs links cGMP to the PKG/β-catenin/APC defect in such cells.

This latter link is further buttressed by the observation that β-catenin itself is reduced when neoplastic cells containing the APC defect or the β-catenin defect are exposed to a SAAND. This reduction in β-catenin is initiated by PKG itself. PKGphosphorylates β-catenin—which is another novel observation associated with this invention. The phosphorylation of β-catenin allows β-catenin to be degraded by ubiquitin-proteasomal system.

This phosphorylation of β-catenin by PKG is important in neoplastic cells because it circumvents the effect of the APC and β-catenin mutations. The mutated APC protein affects the binding of the β-catenin bound to the mutant APC protein, which change in binding has heretofore been thought to prevent the phosphorylation of β-catenin by GSK-3b kinase. In the case of mutant β-catenin, an elevation of PKG activity also allows the mutant β-catenin to be phosphorylated. By elevating PKG activity in neoplasia with cGMP-PDE inhibition allows for a different way of β-catenin phosphorylation (leading to its degradation) in neoplastic cells containing either type of mutation.

In short, these findings not only lead to new pharmaceutical screening methods to identify further SAAND candidate compounds, but also buttress the role of cGMP-specific PDE inhibition in therapeutic approaches to neoplasia. This observation may also explain the unexpectedly broad range of neoplasias SAANDs can inhibit since both neoplasia with and without the APC defect can be treated, as explained above.

Thus, in selecting compounds potentially useful as antineoplastics, ascertaining whether such compounds increase PKG activity in neoplastic cells is useful in the selecting process. By "selecting a compound for treatment of a neoplasia to be treated" we mean not only selecting for further in vitro study in pharmaceutical discovery, but also for further in vivo study and later clinical use against various types of neoplasias (e.g., neoplasias that exhibit either the APC mutation and/or the β-catenin mutation). This methodology can assist both in the selection or screening process during pharmaceutical discovery, but also in clinical trials and in the clinic to help ascertain whether a compound will be useful in treating a particular neoplasia.

As used herein, the term "precancerous lesion" includes syndromes represented by abnormal neoplastic, including dysplastic, changes of tissue. Examples include dysplastic growths in colonic, breast, prostate or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, lung, prostatic dysplasia, prostatic intraneoplasia, breast and/or skin and related conditions (e.g., actinic keratosis), whether the lesions are clinically identifiable or not.

As used herein, the terms "carcinoma" or "cancer" refers to lesions which are cancerous. Examples include malignant melanomas, breast cancer, prostate cancer and colon cancer. As used herein, the terms "neoplasia" and "neoplasms" refer to both cancerous and pre-cancerous lesions.

Also disclosed is a novel assay for PKG activity, which is used in the screening methods of this invention, but also has more general usefulness in assaying for PKG activity for other purposes (e.g., for studying the role of PKG in normal cellular function). For explanation purposes, it is useful to describe the PKG assay first, before describing how PKG activity can be useful in drug evaluation in ascertaining whether a compound is potentially useful in the treatment of neoplasia.

The Novel PKG Assay

The novel PKG assay of this invention involves binding to a solid phase plural amino acid sequences, each of which contain at least the cGMP binding domain and the phosphorylation site of phosphodiesterase type 5 ("PDE5"). That sequence is known and described in the literature below. Preferably, the bound PDE5 sequence does not include the catalytic domain of PDE5 as described below. One way to bind the PDE5 sequences to a solid phase is to express those sequences as a fusion protein of the PDE5 sequence and one member of an amino acid binding pair, and chemically link the other member of that amino acid binding pair to a solid phase (e.g., beads). One binding pair that can be used is glutiathione S-transferase ("GST") and glutathione ("GSH"), with the GST being expressed as a fusion protein with the PDE5 sequence described above, and the GSH bound covalently to the solid phase. In this fashion, the PDE5 sequence/GST fusion protein can be bound to a solid phase simply by passing a solution containing the fusion protein over the solid phase, as described below.

RT-PCR method is used to obtain the cGB domain of PDE5 with forward and reverse primers designed from bovine PDE5A cDNA sequence (McAllister-Lucas L. M. et al, *J. Biol. Chem.* 268, 22863–22873, 1993) and the selection among PDE 1-10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-PDE5). The synthesized cGB-PDE5 nucleotide fragment codes for 494 amino acids with 97% similarity to bovine PDE5A. It is then cloned into pGEX-5X-3 glutathione-S-transferase (GST) fusion vector (Pharmacia Biotech)with tac promoter, and EcoRI and XhoI cut sites. The fusion vector is then transfected into *E. Coli* BL21 (DE3) bacteria (Invitrogen). The transfected BL21 bacteria is grown to log phase and then IPTG is added as an inducer. The induction is carried at 20° C. for 24 hrs. The bacteria are harvested and lysated. The soluble cell lysate is incubated with GSH conjugated Sepharose 4B (GSH-Sepharose 4B). The GST-cGB-PDE5 fusion protein can bind to the GSH-Sepharose beads and the other proteins are washed off from beads with excessive cold PBS.

The expressed GST-cGB-PDE5 fusion protein is displayed on 7.5% SDS-PAGE gel as a 85 Kd protein. It is characterized by its cGMP binding and phosphorylation by protein kinases G and A. It displays two cGMP binding sites and the $K_d$ is 1.6±0.2 $\mu$M, which is close to $K_d$=1.3 $\mu$M of the native bovine PDE5. The GST-cGB-PDE5 on GSH conjugated sepharose beads can be phosphorylated in vitro by cGMP-dependent protein kinase and cAMP-dependent protein kinase A. The $K_m$ of GST-cGB-PDE5 phosphorylation by PKG is 2.7 $\mu$M and Vmax is 2.8 $\mu$M, while the $K_m$ of BPDEtide phosphorylation is 68 $\mu$M. The phosphorylation by PKG shows one molecular phosphate incorporated into one GST-cGB-PDE5 protein ratio.

To assay a liquid sample believed to contain PKG using the PDE5-bound solid phase described above, the sample and the solid phase are mixed with phosphorylation buffer containing $^{32}$P-γ-ATP. The solution is incubated for 30 minutes at 30° C. to allow for phosphorylation of the PDE5 sequence by PKG to occur, if PKG is present. The solid phase is then separated from solution (e.g., by centrifugation or filtration) and washed with phosphate-buffered saline ("PBS") to remove any remaining solution and to remove any unreacted $^{32}$P-γ-ATP.

The solid phase can then be tested directly (e.g., by liquid scintillation counter) to ascertain whether $^{32}$P is incorporated. If it does, that indicates that the sample contained PKG since PKG phosphorylates PDE5. If the PDE5 is bound via fusion protein, as described above, the PDE5-containing fusion protein can be eluted from the solid phase with SDS buffer, and the eluent can be assayed for $^{32}$P incorporation. This is particularly advantageous if there is the possibility that other proteins are present, since the eluent can be processed (e.g., by gel separation) to separate various proteins from each other so that the fusion protein fraction can be assayed for $^{32}$P incorporation. The phosphorylated fusion protein can be eluted from the solid phase with SDS buffer and further resolved by electrophoresis. If gel separation is performed, the proteins can be stained to see the position(s) of the protein, and $^{32}$P phosphorylation of the PDE5 portion of the fusion protein by PKG can be measured by X-ray film exposure to the gel. If $^{32}$P is made visible on X-ray film, that indicates that PKG was present in the original sample contained PKG, which phosphorylated the PDE5 portion of the fusion protein eluted from the solid phase.

Preferably in the assay, one should add to the assay buffer an excess (e.g., 100 fold) of protein kinase inhibitor ("PKI") which specifically and potently inhibits protein kinase A ("PKA") without inhibiting PKG. Inhibiting PKA is desirable since it may contribute to the phosphorylation of the PKG substrate (e.g., PDE5). By adding PKI, any contribution to phosphorylation by PKA will be eliminated, and any phosphorylation detected is highly likely to be due to PKG alone.

A kit can be made for the assay of this invention, which kit contains the following pre-packaged reagents in separate containers:

1. Cell lysis buffer: 50 mM Tris-HCl, 1% NP-40, 150 mM NaCl, 1 mM EDTA, 1 mM $Na_3VO_4$, 1 mM NaF, 500 uM IBMX, proteinase inhibitors.
2. Protein kinase G solid phase substrate: recombinant GST-cGB-PDE5 bound Sepharose 4B (50% slurry).
3. 2x Phosphorylation buffer: $^{32}$P-γ-ATP (3000 mCi/mmol, 5~10 μCi/assay), 10 mM $KH_2PO_4$, 10 mM $K_2HPO_4$, 200 μM ATP, 5 mM $MgCl_2$.
4. Protein Kinase I Disposable containers and the like in which to perform the above reactions can also be provided in the kit.

From the above, one skilled in the analytical arts will readily envision various ways to adapt the assay formats described to still other formats. In short, using at least a portion of PDE5 (or any other protein that can be phosphorylated by PKG), the presence and relative amount (as compared to a control) of PKG can be ascertained by evaluating phosphorylation of the phosphorylatable protein, using a labeled phosphorylation agent.

SAANDs Increase PKG Activity In Neoplastic Cells

Using the PKG assay described above, the following experiments were performed that establish that SAANDs increase PKG activity due either to increase in PKG expression or an increase in cGMP levels (or both) in neoplastic cells treated with a SAAND.

Test Procedures

Two different types of PDE inhibitors were evaluated for their effects on PKG in neoplastic cells. A SAAND, exisulind, was evaluated since it is anti-neoplastic. Also, a non-SAAND classic PDE5 inhibitor, E4021, was evaluated to ascertain whether PKG elevation was simply due to classic PDE5 inhibition, or whether PKG elevation was involved in the pro-apoptotic effect of SAANDs inhibition of PDE5 and the novel PDE disclosed in U.S. patent application Ser. No. 09/173,375 to Liu et al filed Oct. 15, 1998.

To test the effect of cGMP-specific PDE inhibition on neoplasia containing the APC mutation, SW480 colon cancer cells were employed. SW 480 is known to contain the APC mutation. About 5 million SW480 cells in RPMI 5% serum are added to each of 8 dishes:

2–10 cm dishes—30 μL DMSO vehicle control (without drug),

3–10 cm dishes—200 μM, 400 μM, 600 μM exisulind in DMSO, and

3–10 cm dishes—E4021; 0.1 μM, 1 μM and 10 μM in DMSO.

The dishes are incubated for 48 hrs at 37° C. in 5% $CO_2$ incubator.

The liquid media are aspirated from the dishes (the cells will attach themselves to the dishes). The attached cells are washed in each dish with cold PBS, and 200 μL cell lysis buffer (i.e., 50 mM Tris-HCl, 1% NP-40, 150 mM NaCl, 1 mM EDTA, 1 mM $Na_3VO_4$, 1 mM NaF, 500 uM IBMX with proteinase inhibitors) is added to each dish. Immediately after the cell lysis buffer is added, the lysed cells are collected by scraping the cells off each dish. The cell lysate from each dish is transferred to a microfuge tube, and the microfuge tubes are incubated at 4° C. for 15 minutes while gently agitating the microfuge tubes to allow the cells to lyse completely. After lysis is complete, the microfuge tubes are centrifuged full speed (14,000 r.p.m.) for 15 minutes. The supernatant from each microfuge tube is transferred to a fresh microfuge tube.

A protein assay is then performed on the contents of each microfuge tube because the amount of total protein will be greater in the control than in the drug-treated samples, if the drug inhibits cell growth. Obviously, if the drug does work, the total protein in the drug-treated samples should be virtually the same as control. In the above situation, the control and the E-402 1 microfuge tubes needed dilution to normalize them to the high-dose exisulind-treated samples (the lower dose groups of exisulind had to be normalized to the highest dose exisulind sample). Thus, after the protein assays are performed, the total protein concentration of the various samples must be normalized (e.g., by dilution).

For each drug concentration and control, two PKG assays are performed, one with added cGMP, and one without added cGMP, as described in detail below. The reason for performing these two different PKG assays is that cGMP specifically activates PKG. When PKG activity is assayed using the novel PKG assay of this invention, one cannot ascertain whether any increase the PKG activity is due to increased cGMP in the cells (that may be caused by cGMP-specific PDE inhibition) or whether the PKG activity level is due to an increased expression of PKG protein. By determining PKG activity in the same sample both with and without added cGMP, one can ascertain whether the PKG activity increase, if any, is due to increased PKG expression. Thus, if an anti-neoplastic drug elevates PKG activity relative to control, one can establish if the drug-induced increase is due to increased PKG protein expression (as opposed to activation) in the drug-treated sample if (1) the drug-treated sample with extra cGMP exhibits greater PKG activity compared to the control sample with extra cGMP, and (2) the drug-treated sample without extra cGMP exhibits greater PKG activity relative to control.

After, parallel samples with and without added cGMP are prepared, 50 μL of each cell lysate is added to 20 μL of the PDE5/GST solid phase substrate slurry described above. For each control or drug cell lysate sample to be evaluated, the reaction is started by adding phosphorylation buffer containing 10 μCi $^{32}$P-γ-ATP solution (200 μM ATP, 4.5 mM MgCl; 5 mM $KH_2PO_4$; 5 mM $K_2HPO_4$;) to each mixture. The resultant mixtures are incubated at 30° C. for 30 minutes. The mixtures are then centrifuged to separate the solid phase, and the supernatant is discarded. The solid phase in each tube is washed with 700 μL cold PBS. To the solid phase, Laemmli sample buffer (Bio-Rad) (30 μL) is added. The mixtures are boiled for 5 minutes, and loaded onto 7.5% SDS-PAGE. The gel is run at 150 V for one hour. The bands obtained are stained with commassie blue to visualize the 85 Kd GST-PDE5 fusion protein bands, if present. The gel is dried, and the gel is laid on x-ray film which, if the PDE5 is phosphorylated, the film will show a corresponding darkened band. The darkness of each band relates to the degree of phosphorylation.

As shown in FIGS. 18A and 18B, the SAAND exisulind causes PKG activity to increase in a dose-dependent manner in both the samples with added cGMP and without added cGMP relative to the control samples with and without extra cGMP. This is evidenced by the darker appearances of the 85 Kd bands in each of the drug-treated samples. In addition, the SW480 samples treated with exisulind show a greater PKG phosphorylation activity with added cGMP in the assay relative to the samples treated with exisulind alone (i.e. no added cGMP). Thus, the increase in PKG activity in the drug-treated samples is not due only to the activation of PKG by the increase in cellular cGMP when the SAAND inhibits cGMP-specific PDE, the increase in PKG activity in neoplasia harboring the APC mutation is due to increased PKG expression as well.

Also the fact that the E4021-treated SW480 samples do not exhibit PKG activation relative to control (see FIGS.

18A and 18B) shows that the increased PKG activation caused by SAANDs in neoplasia containing the APC mutation is not simply due to inhibition of classic PDE5.

As an analytic technique for evaluating PKG activation, instead of x-ray film exposure as described above, the 85 Kd band from the SDS page can be evaluated for the degree of phosphorylation by cutting the band from the gel, and any $^{32}$P incorporated in the removed band can be counted by scintillation (beta) counter in the $^{32}$P window.

To test the effect of cGMP-specific PDE inhibition on neoplasia containing the β-catenin mutation, HCT116 colon cancer cells were employed. HCT116 is known to contain the β-catenin mutation, but is known not to contain the APC mutation.

The same procedure is used to grow the HCT116 cells as is used in the SW480 procedure described above. In this experiment, only exisulind and controls were used.

The exisulind-treated cells yielded PKG that was phosphorylated to a greater extent than the corresponding controls, indicating that PKG activation occurred in the drug-treated cells that is independent of the APC mutation.

Thus, for the purposes of the present invention, we refer to "reducing β-catenin" in the claims to refer to wild type and/or mutant forms of that protein.

Confirmation of Increased PKG Expression and Decreased β-Catenin in SW 480 By Western Blot As demonstrated above, SAANDs cause an increase in PKG expression and an increase in cGMP level, both of which cause an increase in PKG activity in SAANDs-treated neoplastic cells. This increase in PKG protein expression was further verified by relatively quantative western blot, as described below.

SW480 cells treated with exisulind as described previously are harvested from the microfuge tubes by rinsing once with ice-cold PBS. The cells are lysed by modified RIPA buffer for 15 minutes with agitation. The cell lysate is spun down in a cold room. The supernatants are transferred to fresh microcentrifuge tubes immediately after spinning. BioRad DC Protein Assay (Temecula, Calif.) is performed to determine the protein concentrations in samples. The samples are normalized for protein concentration, as described above.

50 μg of each sample is loaded to 10% SDS gel. SDS-PAGE is performed, and the proteins then are transferred to a nitrocellulose membrane. The blotted nitrocellulose membrane are blocked in freshly prepared TBST containing 5% nonfat dry milk for one hour at room temperature with constant agitation.

A goat-anti-PKG primary antibody is diluted to the recommended concentration/dilution in fresh TBST/5% nonfat dry milk. The nitrocellulose membrane is placed in the primary antibody solution and incubated one hour at room temperature with agitation. The nitrocellulose membrane is washed three times for ten minutes each with TBST. The nitrocellulose membrane is incubated in a solution containing a secondary POD conjugated rabbit anti-goat antibody for 1 hour at room temperature with agitation. The nitrocellulose membrane is washed three times for ten minutes each time with TBST. The detection is performed by using Boehringer Mannheim BM blue POD substrate.

As graphically illustrated in FIG. 19, exisulind causes the drop of β-catenin and the increase of PKG, which data were obtained by Western blot. SW480 cells were treated with exisulind or vehicle (0.1% DMSO) for 48 hours. 50 μg supernatant of each cell lysates were loaded to 10% SDS-gel and blotted to nitrocellulose membrane, and the membrane was probed with rabbit-anti-β-catenin and rabbit anti-PKG antibodies.

SAANDs Reduce β-Catenin Levels in Neoplastic Cells

This observation was made by culturing SW480 cells with either 200–600 μM exisulind or vehicle (0.1% DMSO). The cells are harvested 48 hours post treatment and processed for immunoblotting. Immuno-reactive protein can be detected by western blot. Western blot analysis demonstrated that expression of β-catenin was reduced by 50% in the exisulind-treated cells as compared to control. These results indicate that β-catenin is reduced by SAANDs treatment. Together with the results above establishing PKG activity increases with such treatment and the results below establishing that β-catenin is phosphorylated by PKG, these results indicate that the reduction of β-catenin in neoplastic cells is initiated by activation of PKG. Thus, using PKG activity in neoplasia as a screening tool to select compounds as anti-neoplastics is useful.

The Phosphorylation of β-catenin By PKG

In vitro PKG phosphorylates β-catenin. The experiment that established this involves immunoprecipitating the β-catenin-containing complex from SW480 cells (not treated with any drug) in the manner described below under "β-catenin immunoprecipitation" The immunoprecitated complex, while still trapped on the solid phase (i.e., beads) is mixed with $^{32}$P-γ-ATP and pure PKG (100 units). Corresponding controls with out added PKG are prepared.

The protein is released from the solid phase by SDS buffer, and the protein-containing mixture is run on a 7.5% SDS-page gel. The running of the mixture on the gell removes excess $^{32}$P-γ-ATP from the mixture. Any $^{32}$P-γ-ATP detected in the 93 Kd β-catenin band, therefore, is due to the phosphorylation of the β-catenin. Any increase in $^{32}$P-γ-ATPdetected in the 93 Kd β-catenin band treated with extra PKG relative to the control without extra PKG, is due to the phosphorylation of the catenin in the treated band by the extra PKG.

The results we obtained were that there was a noticeable increase in phosphorylation in the band treated with PKG as compared to the control, which exhibited minimal, virtually undetectable phosphorylation. This result indicates that β-catenin can be phosphorylated by PKG.

The Phosphorylation of Mutant β-catenin By PKG

The same procedure described in the immediately preceding section was performed with HCT116 cells, which contain no APC mutation, but contain a β-catenin mutation. The results of those experiments also indicate that mutant β-catenin is phosphorylated by PKG.

Thus, for the purposes of the present invention, we refer to the phosphorylation of β-catenin in the claims to refer to the phosphorylation of wild type and/or mutant forms of that protein.

β-Catenin Precipitates With PKG

Supernatants of both SW480 and HCT116 cell lysates are prepared in the same way described above in the Western Blot experiments. The cell lysate are pre-cleared by adding 150 μl of protein A sepharose bead slurry (50%) per 500 μg of cell lysate and incubating at 4° C. for 10 minutes on a tube shaker. The protein A beads are removed by centrifugation at 14,000× g at 4° C. for 10 minutes. The supernatant are transferred to afresh centrifuge tube. 10 μg of the rabbit polyclonal anti-β-catenin antibody (Upstate Biotechnology, Lake Placid, N.Y.) are added to 500 μg of cell lysate. The cell lysate/antibody mixture is gently mixed for 2 hours at 4° C. on a tube shaker. The immunocomplex is captured by adding 150 μl protein A sepharose bead slurry (75 μl packed beads) and by gently rocking the mixture on a tube shaker for overnight at 4° C. The sepharose beads are collected by pulse centrifugation (5 seconds in the microcentrifuge at 14,000 rpm). The supernatant fraction is discarded, and the beads are washed 3 times with 800 µl ice-cold PBS buffer. The sepharose beads are resuspended in 150 µl 2× sample buffer and mixed gently. The sepharose beads are boiled for 5 minutes to dissociate the immunocomplexes from the beads. The beads are collected by centrifugation and SDS-PAGE is performed on the supernatant.

A western blot is run on the supernatant, and the membrane is then probed with an rabbit anti β-catenin antibody. Then the membrane is washed 3 times for 10 minutes each with TBST to remove excess anti β-catenin antibody. A goat-anti-rabbit antibody horseradish peroxidase conjugate is added, followed by 1 hour incubation at room temperature. When that is done, one can visualize the presence of β-catenin with an HRPO substrate. In this experiment, we could clearly visualize the presence of β-catenin.

To detect PKG on the same membrane, the anti-β-catenin antibody conjugate is first stripped from the membrane with a 62 mM tris-HCl buffer (pH 7.6) with 2% SDS and 100 µM 2β-mercaptoethanol in 55° C. water bath for 0.5 hour. The stripped membrane is then blocked in TBST with 5% non-fat dried milk for one hour at room temperature while agitating the membrane. The blocked, stripped membrane is then probed with rabbit polyclonal anti-PKG antibody (Calbiochem, LaJolla, Calif.), which is then probed with goat-anti-rabbit antibody conjugated with HRPO. The presence of PKG on the membrane is visualized with an HRPO substrate. In this experiment, the PKG was, in fact, visualized. Given that the only proteins on the membrane are those that immunoprecipitated with β-catenin in the cell supernatants, this result clearly establishes that PKG was physically linked to the protein complex containing the β-catenin in the cell supernatants.

The same Western blot membrane was also probed after stripping with anti-GSK3β antibody to ascertain whether it also co-precipitated with β-catenin. In that experiment, we also detected GSK3 on the membrane, indicating that the GSK3 precipitated with the GSK3 and PKG, suggesting that the three proteins may be part of the same complex. Since GSK3β and β-catenin form part of the APC complex in normal cells, this that PKG may be part of the same complex, and may be involved in the phosphorylation of β-catenin as part of that complex.

Screening for cGMP PDE Inhibition

In the course of researching why some PDE5 inhibitors induced apoptosis while others did not, a form of cyclic GMP-specific phosphodiesterase was found that had not previously been described. The new PDE was disclosed in U.S. patent application Ser. No. 09/173,375 filed Oct. 15, 1998. This new phosphodiesterase activity was previously uncharacterized, possibly because it is expressed only in neoplastic tissue, or perhaps because it is a mutation of a known/characterized PDE. This new PDE is useful in screening pharmaceutical compounds for desirable anti-neoplastic properties.

In its broadest aspects, this new PDE is characterized by having:

(a) cGMP specificity over cAMP (b) positive cooperative kinetic behavior in the presence of cGMP substrate;

(c) submicromolar affinity for cGMP; and (d) insensitivity to incubation with purified cGMP-dependent protein kinase Other characteristics of this novel PDE include: it has a reduced sensitivity to inhibition by zaprinast and E4021, it can be separated from classical PDE5 activity by anion-exchange chromatography, it is not activated by calcium/calmodulin, and it is insensitive to rolipram, vinpocetine and indolodan.

This invention can include screening and/or selecting compounds for their ability to treat and prevent neoplasia with the aid of the new PDE. The compounds so identified can have minimal side effects attributable to COX inhibition and other non-specific interactions. The compounds of interest can be tested by exposing the novel PDE described above to the compounds, and if a compound inhibits this novel PDE, the compound is then further evaluated for its anti-neoplastic properties.

One further aspect of this invention, therefore, involves a method to identify a compound effective for treating neoplasia that includes ascertaining the compound's inhibition of this novel PDE and/or its inhibition of COX. Preferably, the screening method of this invention further includes determining whether the compound inhibits the growth of tumor cells in a cell culture.

By screening compounds in this fashion, potentially beneficial and improved compounds for treating neoplasia can be identified more rapidly and with greater precision than possible in the past. Further benefits will be apparent from the detailed description that follows.

The Novel cGMP-Specific Phosphodiesterase

A. Its Isolation

The isolated cGMP-specific phosphodiesterase was prepared from the human carcinoma cell line commonly referred to as SW480 available from the American Tissue Type Collection in Rockville, Md., U.S.A. SW480 is a human colon cancer cell line that originated from moderately differentiated epithelial adenocarcinoma. It has also been isolated from neoplasias of the breast (i.e., HTB-26) and prostate (i.e., LNCAP line).

To isolate the novel phosphodiesterase from SW480, approximately four hundred million SW480 cells at confluence were scraped from 150 $cm^2$ tissue culture dishes after two washes with 10 ml cold PBS and pelleted by centrifugation. The cells were resuspended in homogenization buffer (20 ml TMPI-EDTA-Triton pH 7.4: 20 mM Tris-HOAc, 5 mM $MgAc_2$, 0.1 mM EDTA, 0.8% Triton-100, 10µM Benzamidine, 10 µM TLCK, 2000 U/mL Aprotinin, 2 µM Leupeptin, 2 µM Pepstatin A) and homogenized on an ice bath using a polytron tissumizer (three times, 20 seconds/pulse). The homogenized material was centrifuged at 105,000 g for 60 minutes at 4° C. in a Beckman L8 ultracentrifuge, and the supernatant was diluted with TMPI-EDTA (60 ml) and applied to a 10-milliliter DEAE-Trisacryl M column pre-equilibrated with TMPI-EDTA buffer. The loaded column was washed with 60 mL of TM-EDTA, and PDE activities were eluted with a 120 ml linear gradient of NaOAc (0–0.5 M) in TM-EDTA, at a flow rate of 0.95 ml/minute, 1.4 ml/fraction. Eighty fractions were collected and assayed for cGMP hydrolysis immediately (i.e. within minutes). FIG. 1. shows the column's elution profile, revealing two initial peaks of cGMP PDE activity, A and B, which were eluted by 40–50 mM and 70–80 mM NaOAC, respectively. As explained below, peak A is PDE5, whereas peak B is the novel phosphodiesterase.

Cyclic nucleotide PDE activity of each fraction was determined using the modified two-step radioisotopic method of Thompson et al. (Thompson W. J., et al., Adv Cyclic Nucleotide Res 10: 69–92, 1979), as further described below. The reaction was in 400 µl containing Tris-HCl (40 mM; pH 8.0), $MgCl_2$ (5 mM), 2-mercaptoethanol (4 mM), bovine serum albumin (30 µg), cGMP (0.25 µM–5 µM) with constant tritiated substrate (200,000 cpm). The incubation time was adjusted to give less than 15% hydrolysis. The mixture was incubated at 30° C. followed by boiling for 45 seconds to stop the reaction.

Then the mixture was cooled, snake venom (50 kg) added, and the mixture was incubated at 30° C. for 10 minutes. MeOH (1 ml) was added to stop the reaction, and the mixture was transferred to an anion-exchange column (Dowex 1-X8, 0.25 ml resin). The eluant was combined with a second ml of MeOH, applied to the resin, and after adding 6 ml scintillation fluid tritium activity was measured using a Beckman LS 6500 for one minute.

Figure 2:
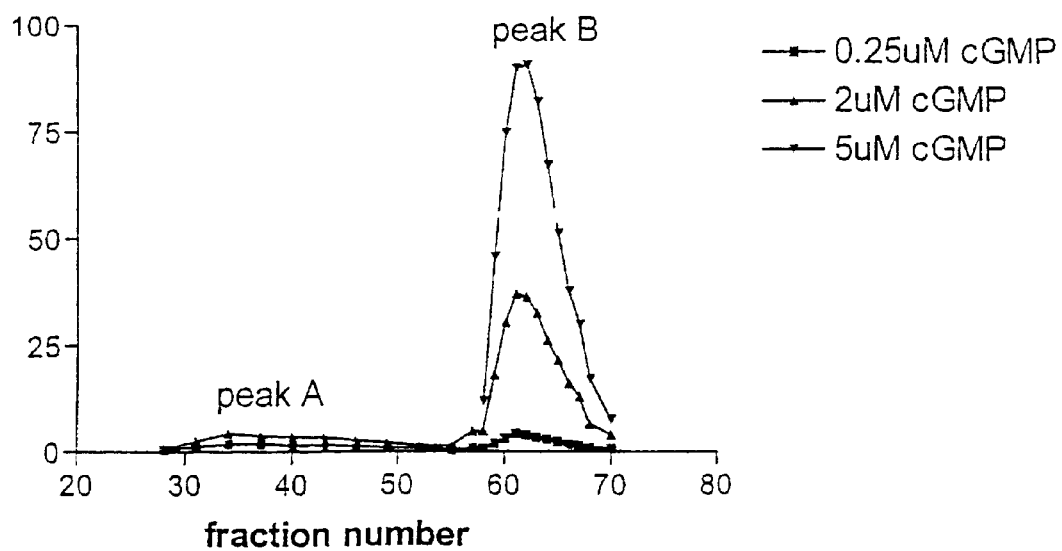
FIG. 2 is a graph of cGMP activities of the reloaded cGMP phosphodiesterases obtained from SW480 neoplastic cells, as assayed from the eluent of a DEAE-Trisacryl M column.

To fractionate cGMP hydrolytic activity of peaks A and B further, fractions 15 to 30 of the original 80 were reloaded onto the DEAE-Trisacryl M column and eluted with a linear gradient of NaOAc (0–0.5 M) in TM-EDTA. Fractions were again immediately assayed for cGMP hydrolysis (using the procedure described above with 0.2, 2, 5 $\mu$M substrate), the results of which are graphically presented in FIG. 2. One novel observation about peak B illustrated in FIG. 2 is that increasing substrate concentration of cGMP dramatically enhanced activity when contrasted to peak A. Peak A activity shows apparent substrate saturation of high affinity catalytic sites.

B. cGMP-Specifity of PDE Peaks A and B

Each fraction from the DEAE column was also assayed for cGMP-hydrolysis activity (0.25 $\mu$M cGMP) in the presence or absence of $Ca^{++}$, or $Ca^{++}$-CaM and/or EGTA and for cAMP (0.25 $\mu$M cAMP) hydrolysis activity in the presence or absence of 5 $\mu$M cGMP. Neither PDE peak A and peak B (fractions 5–22; see FIG. 1) hydrolyzed cAMP significantly, establishing that neither was a cAMP hydrolysing gene family of PDE (i.e. a PDE 1, 2, 3).

$Ca^{++}$(with or without calmodulin) failed to activate either cAMP or cGMP hydrolysis activity of either peak A or B, and cGMP failed to activate or inhibit cAMP hydrolysis. Such results establish that peaks A and B constitute cGMP-specific PDEs but not PDE1, PDE2, PDE3 or PDE4.

For PDE peak B, as discussed below, cyclic GMP activated the cGMP hydrolytic activity of the enzyme, but did not activate any cAMP hydrolytic activity. This reveals that PDE peak B—the novel phosphodiesterase—is not a cGMP-stimulated cAMP hydrolysis ("cGS") or among the PDE2 family isoforms because the known isoforms of PDE2 hydrolyze both cGMP and cAMP.

C. Peak A is A PDE5, But Peak B—A New cGMP-Specific PDE-is Not

To characterize any PDE isoform, kinetic behavior and substrate preference should be assessed.

Peak A showed typical "PDE5" characteristics. For example, the Km of the enzyme for cGMP was 1.07 $\mu$M, and Vmax was 0.16 nmol/min/mg. In addition, as discussed below, zaprinast ($IC_{50}$=1.37 $\mu$M) and E4021 ($IC_{50}$=3 nM) and sildenafil inhibited activity of peak A. Further, zaprinast showed inhibition for cGMP hydrolysis activity of peak A, consistent with results reported in the literature.

Figure 3:
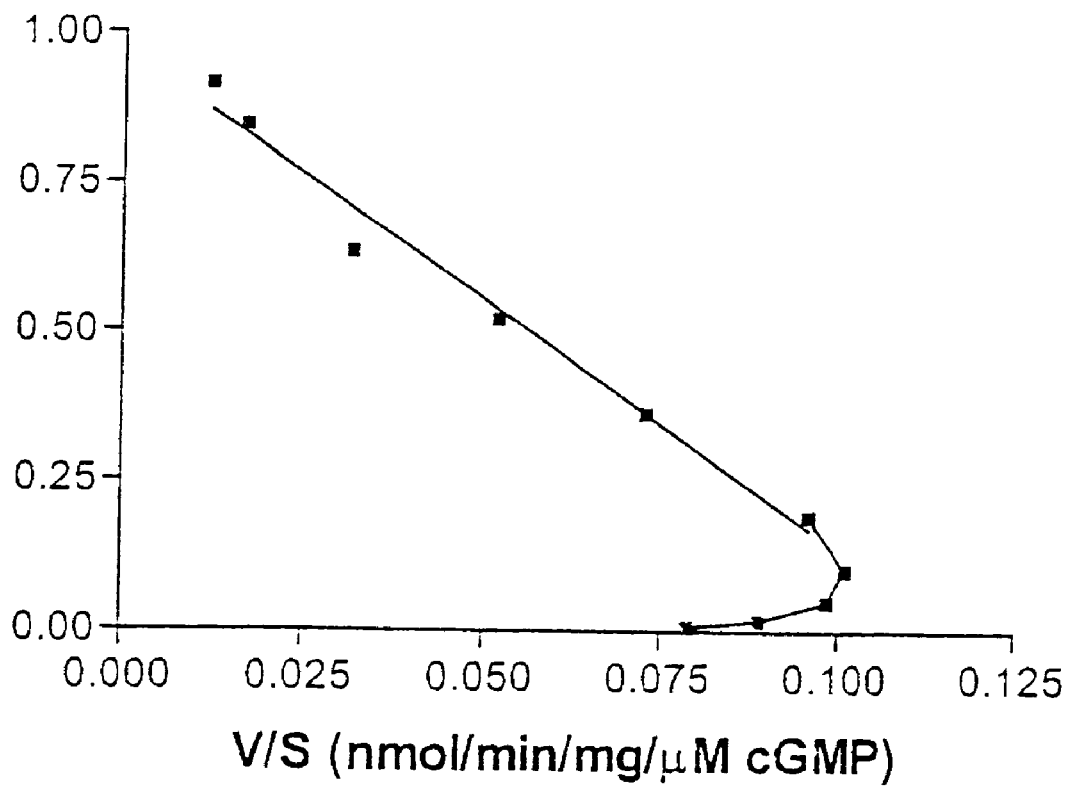
FIG. 3 is a graph of the kinetic behavior of the novel PDE of this invention.

PDE Peak B showed considerably different kinetic properties as compared to PDE peak A. For example, in Eadie-Hofstee plots of Peak A, cyclic GMP hydrolysis shows single line with negative slope with increasing substrate concentrations, indicative of Michaelis-Menten kinetic behavior. Peak B, however, shows the novel property for cGMP hydrolysis in the absence of cAMP of a decreasing (apparent $K_m$=8.4), then increasing slope ($K_m$<1) of Eadie-Hotfstee plots with increasing cGMP substrate (see, FIG. 3). Thus, this establishes Peak B's submicromolar affinity for cGMP (i.e., where $K_m$<1).

Consistent with the kinetic studies (i.e. FIG. 3) and positive-cooperative kinetic behavior in the presence of cGMP substrate, was the increased cGMP hydrolytic activity in the presence of increasing concentrations of cGMP substrate. This was discovered by comparing 0.25 $\mu$M, 2 $\mu$M and 5 $\mu$M concentrations of cGMP in the presence of PDE peak B after a second DEAE separation to rule out cAMP hydrolysis and to rule out this new enzyme being a "classic" PDE5. Higher cGMP concentrations evoked disproportionately greater cGMP hydrolysis with PDE peak B, as shown in FIG. 2.

These observations suggest that cGMP binding to the peak B enzyme causes a conformational change in the enzyme.

D. Zaprinast- and Sildenafil-Insensitivity of PDE Peak B Relative to Peak A, and Their Effects on Other PDE Inhibitors Different PDE inhibitors were studied using twelve concentrations of drug from 0.01 to 100 $\mu$M and substrate concentration of 0.25 $\mu$M $^3$H-cGMP. $IC_{50}$ values were calculated with variable slope, sigmoidal curve fits using Prism 2.01 (GraphPad). The results are shown in Table 2. While compounds E4021 and zaprinast inhibited peak A, (with high affinities) $IC_{50}$ values calculated against peak B are significantly increased (>50 fold). This confirms that peak A is a PDE5. These data further illustrate that the novel PDE of this invention is, for all practical purposes, zaprinast-insensitive and E4021-insensitive.

TABLE 2

Comparison of PDE Inhibitors Against Peak A and Peak B (cGMP Hydrolysis)

| Compound | PDE Family Inhibitor | $IC_{50}$ Peak A ($\mu$M) | $IC_{50}$ Peak B ($\mu$M) | Ratio ($IC_{50}$ Peak A/Peak B) |
|---|---|---|---|---|
| E4021 | 5 | 0.003 | 8.4 | 0.0004 |
| Zaprinast | 5 | 1.4 | >30 | <0.05 |
| Compound E | 5 and others | 0.38 | 0.37 | 1.0 |
| Sulindac sulfide | 5 and others | 50 | 50 | 1.0 |
| Vinpocetine | 1 | >100 | >100 | |
| EHNA | 2,5 | >100 | 3.7 | |
| Indolidan | 3 | 31 | >100 | <0.31 |
| Rolipram | 4 | >100 | >100 | |
| Sildenafil | 5 | .0003 | >10 | <.00003 |

By contrast, sulindac sulfide and Compound E and competitively inhibited both peaks A and B phosphodiesterases at the same potency ($IC_{50}$=0.38 $\mu$M for PDE peak A; 0.37 $\mu$M for PDE peak B).

There is significance for the treatment of neoplasia and the screening of useful compounds for such treatment in the fact that peak B is zaprinast-insensitive whereas peaks A and B are both sensitive to sulindac sulfide and Compound E. We have tested zaprinast, E4021 and sildenafil to ascertain whether they induce apoptosis or inhibit the growth of neoplastic cells, and have done the same for Compound E. As explained below, zaprinast does not have significant apoptosis-inducing or growth-inhibiting properties, whereas sulindac sulfide and Compound E are precisely the opposite. In other words, the ability of a compound to inhibit both PDE peaks A and B correlates with its ability to induce apoptosis in neoplastic cells, whereas if a compound (e.g., zaprinast) has specificity for PDE peak A only, that compound will not induce apoptosis.

E. Insensitivity of PDE Peak B To Incubation With cGMP-Dependent Protein Kinase G Further differences between PDE peaks A and B were observed in their respective cGMP-hydrolytic activities in the presence of varying concentrations of cGMP-dependent protein kinase G (which phosphorylates typical PDE5). Specifically, peak A and peak B fractions were incubated with different concentrations of protein kinase G at 30° C. for 30 minutes. Cyclic GMP hydrolysis of both peaks has assayed after phosphorylation was attempted. Consistent with previously published information about PDE5, Peak A showed increasing cGMP hydrolysis activity in response to protein kinase G incubation, indicating that Peak A was phosphorylated. Peak B was unchanged, however (i.e., was not phosphorylated and insensitive to incubation with cGMP-dependent protein kinase G). These data are consistent with Peak A being a PDE5 family isoform and Peak B being a novel cGMP PDE.

F. Screening Pharmaceutical Compositions Using The New PDE

1. In General

The novel PDE is useful to identify compounds that can be used to treat or prevent neoplasms, and that are not characterized by serious side effects.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a test compound is important to the discovery of a relevant target for pharmaceutical therapy. Screening assays based on this technology can be combined with other tests to determine which compounds have growth inhibiting and pro-apoptotic activity.

This is the product of several important discoveries. First, it was discovered that desirable inhibitors of tumor cell growth induce premature death of cancer cells by apoptosis (see, Piazza, G. A., et al., *Cancer Research*, 55(14), 3110–16, 1995). Second, it was unexpectedly discovered compounds that can selectively induce apoptosis without substantial COX inhibition also inhibit PDE5. In particular, and contrary to leading scientific studies, desirable compounds for treating neoplastic lesions inhibit PDE5 (EC 3.1.4.17). PDE5 is one of at least ten gene families of phosphodiesterase. PDE5 and the novel PDE of this invention are unique in that they selectively degrade cyclic GMP and not cAMP, while the other families of PDE selectively degrade/hydrolyze cAMP and not cGMP or non-selectively degrade both cGMP and cAMP. Preferably, desirable compounds used to treat neoplasia do not substantially inhibit non-selective or cAMP degrading phosphodiesterase types.

2. COX Screening

One preferred embodiment of the present invention involves determining the cyclooxygenase inhibition activity of a given compound, and determining the cGMP specific PDE inhibitory activity of the compound. The test compounds are scored for their probable ability to treat neoplastic lesions either directly or indirectly by comparing their activities against known compounds useful for treating neoplastic lesions. A standard compound that is known to be effective for treating neoplastic lesions without causing gastric irritation is 5-fluoro-2-methyl-1-(p-methylsulfonylbenzylidene)-3-indenylacetic acid ("exisulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit (cGMP-specific PDEs, such as 1-(3-chloroanilino)-4-phenyphthalazine ("MY5445").

As used herein, the abbreviation PG represents prostaglandin; PS represents prostaglandin synthetase; $PGE_2$ represents prostaglandin E2; PDE represents phosphodiesterase; COX represents cyclooxygenase; cyclic nucleotide, RIA represents—radioimmunoassay.

COX inhibition by a test compound can be determined by either of two methods. One method involves measuring $PGE_2$ secretion by intact HL-60 cells following exposure to the compound being screened. The other method involves measuring the activity of purified cyclooxygenases (COXs) in the presence of the compound. Both methods involve protocols previously described in the literature, but preferred protocols are set forth below.

Compounds of can be evaluated to determine whether they inhibit the production of prostaglandin $E_2$ ("$PGE_2$"), by measuring $PGE_2$. Using an enzyme immunoassay (EIA) kit for $PGE_2$, such as commercially available from Amersham, Arlington Heights, Ill. U.S.A. Suitable cells include those that make an abundance of PG, such as HL-60 cells. HL-60 cells are human promyelocytes that are differentiated with DMSO into mature granulocytes (See, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.*, 149:969–974, 1979). These differentiated cells produce $PGE_2$ after stimulation with a calcium ionophore, A23187 (see, Kargman, S., Prasit, P. and Evans, J. F., "Translocation of HL-60 Cell 5-Lipoxygenase", *J. Biol. Chem.*, 266: 23745–23752, 1991). HL-60 are available from the American Type Culture Collection (ATCC:CCL240). They can be grown in a RPMI 1640 medium supplemented with 20% heat-inactivated fetal bovine serum, 50 U/ml penicillin and 50 ,g/ml streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at a concentration of $3\times10^6$ cells/mi.

The differentiated HL-60 cells ($3\times10^6$ cells/ml) are incubated for 15 minutes at 37° C. in the presence of the compounds tested at the desired concentration. Cells are then stimulated by A23187 ($5\times10^{-6}$ M) for 15 minutes. $PGE_2$ secreted into the external medium is measured as described above.

As indicated above, a second method to assess COX inhibition of a test compound is to measure the COX activity in the presence of a test compound. Two different forms of cyclooxygenase (COX-I and COX-2) have been reported in the literature to regulate prostaglandin synthesis. COX-2 represents the inducible form of COX while COX-I represents a constitutive form. COX-I activity can be measured using the method described by Mitchell et al. ("Selectivity of Nonsteroidal Anti-inflammatory Drugs as Inhibitors of Constitutive and Inducible Cyclooxygenase," *Proc. Natl. Acad. Sci. USA.*, 90:11693–11697, 1993, which is incorporated herein by reference) using COX-I purified from ram seminal vesicles as described by Boopathy & Balasubramanian, "Purification And Characterization Of Sheep Platelet Cyclooxygenase" (*Biochem. J.*, 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 minutes with 100 PM arachidonic acid (Sigma Chemical Co.), cofactors (such as 1.0 mM glutathione, 1.0 mM hydroquinone, 0.625 $\mu$M hemoglobin and 1.25 mM $CaCl_2$ in 100 mM Tris-HCl, pH 7.4) and the drug to be tested. Following incubation, the reaction can be terminated with trichloroacetic acid. After stopping the reaction by adding thiobarbituric acid and malonaldehyde, enzymatic activity can then be measured spectrophotometrically at 530 nm.

Obviously, a compound that exhibits minimal COX-I or COX-2 inhibitory activity in relation to its greater PDE5/novel PDE inhibitory activity may be a desirable test compound.

The amount of COX inhibition is determined by comparing the activity of the cyclooxygenase in the presence and absence of the test compound. Residual (i.e., less than about 25%) or no COX inhibitory activity at a concentration of about 100 $\mu$M is indicative that the compound should be evaluated further for usefulness for treating neoplasia. Preferably, the $IC_{50}$ should be greater than 1000 $\mu$M for the compound to be further considered potential use.

3. Determining Phosphodiesterase Inhibition Activity

Compounds can be screened for inhibitory effect on the activity of the novel phosphodiesterase of this invention using either the enzyme isolated as described above, a recombinant version, or using the novel PDE together with PDE5. Alternatively, cyclic nucleotide levels in whole cells are measured by RIA and compared to untreated and zaprinast-treated cells.

Phosphodiesterase activity can be determined using methods known in the art, such as a method using radioactive $^3$H cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 $\mu$M; 100,000 cpm; containing 40 mM Tris-HCl (pH 8.0), 5 mM $MgCl_2$ and 1 mg/ml BSA) is mixed with the drug to be tested in a total volume of 400 $\mu$l. The mixture is incubated at 30° C. for 10 minutes with isolated PDE of this invention. Reactions are terminated, for example, by boiling the reaction mixture for 75 seconds. After cooling on ice, 100 $\mu$l of 0.5 mg/ml snake venom (O. Hannah venom available from Sigma) is added and incubated for 10 minutes at 30° C. This reaction is then terminated by the addition of an alcohol, e.g. 1 ml of 100% methanol. Assay samples are applied to 1 ml Dowex 1-X8 column; and washed with 1 ml of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterase of this invention is reflected by an increase in cGMP in neoplastic cells exposed to a compound being screened. The amount of PDE activity can be determined by assaying for the amount of cyclic GMP in the extract of treated cells using radioimmunoassay (RIA). In this procedure, HT-29 or SW-480 cells are plated and grown to confluency. As indicated above, SW-480 contains both PDE5 and the novel PDE of this invention, so when PDE activity is evaluated in this fashion, a combined cGMP hydrolytic activity is assayed simultaneously. The test compound is then incubated with the cell culture at a concentration of compound between about 200 $\mu$M to about 200 $\mu$M. About 24 to 48 hours thereafter, the culture media is removed from the cells, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). Iodinated ligands (tyrosine methyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition, the culture media may be acidified, frozen (−70° C.) and also analyzed for cGMP and cAMP.

In addition to observing increases in the content of cGMP in neoplastic cells caused by desirable test compounds, decreases in content of cAMP have also been observed. It has been observed that a particularly desirable compound (i.e. one that selectively induces apoptosis in neoplastic cells, but not substantially in normal cells) follows a time course consistent with cGMP-specific PDE inhibition as one initial action resulting in an increased cGMP content within minutes. Secondarily, treatment of neoplastic cells with a desirable anti-neoplastic compound leads to decreased cAMP content within 24 hours. The intracellular targets of drug actions are being studied further, but current data support the concept that the initial rise in cGMP content and the subsequent fall in cAMP content precede apoptosis in neoplastic cells exposed to desirable compounds.

The change in the ratio of the two cyclic nucleotides may be a more accurate tool for evaluating desirable cGMP-specific phosphodiesterase inhibition activity of test compounds, rather than measuring only the absolute value of cGMP, only cGMP-specific phosphodiesterase inhibition, or only the level of cGMP hydrolysis. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure intact cell cAMP, $^3$H-adenine prelabeling is used according to published procedures (Whalin M. E., R. L. Garrett Jr., W. J. Thompson, and S. J. Strada, "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell prelabeling according to published procedures (Reynolds, P. E., S. J. Strada and W. J. Thompson, "Cyclic GMP accumulation in pulmonary microvascular endothelial cells measured by intact cell prelabeling," *Life Sci.*, 60:909–918, 1997, which is incorporated herein by reference).

The PDE inhibitory activity effect of a test compound can also be determined from a tissue sample. Tissue biopsies from humans or tissues from anestesized animals are collected from subjects exposed to the test compound. Briefly, a sample of tissue is homogenized in 500 µl of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 µl of assay buffer. The amount of cGMP-specific inhibition is determined by assaying for the amount of cyclic nucleotides using RIA procedures as described above.

The amount of inhibition is determined by comparing the activity of the novel PDE in the presence and absence of the test compound. Inhibition of the novel PDE activity is indicative that the compound is useful for treating neoplasia. Significant inhibitory activity greater than that of the benchmark, exisulind, preferably greater than 50% at a concentration of 10 µM or below, is indicative that a compound should be further evaluated for antineoplastic properties. Preferably, the IC$_{50}$ value for the novel PDE inhibition should be less than 50 µM for the compound to be further considered for potential use.

4. Determining Whether A Compound Reduces the Number of Tumor Cells

In an alternate embodiment, the screening method of the present invention involves further determining whether the compound reduces the growth of tumor cells. Various cell lines can be used in the sample depending on the tissue to be tested. For example, these cell lines include: SW-480—colonic adenocarcinoma; HT-29—colonic adenocarcinoma; A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

A compound's ability to inhibit tumor cell growth can be measured using the HT-29 human colon carcinoma cell line obtained from ATCC (Bethesda, Md.). HT-29 cells have previously been characterized as a relevant colon tumor cell culture model (Fogh, J., and Trempe, G. *In: Human Tumor Cells in Vitro*, J. Fogh (eds.), Plenum Press, New York, pp. 115–159, 1975). HT-29 cells are maintained in RPMI media supplemented with 5% fetal bovine calf serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of test compound. Each determination of cell number involved six replicates. After six days in culture, the cells are fixed by the addition of cold trichloroacetic acid to a final concentration of 10% and protein levels are measured using the sulforhodamine B (SRB) calorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 50% at a dose of 100 µM or below is further indicative that the compound is useful for treating neoplastic lesions. Preferably, an IC$_{50}$ value is determined and used for comparative purposes. This value is the concentration of drug needed to inhibit tumor cell growth by 50% relative to the control. Preferably, the IC$_{50}$ value should be less than 100µM for the compound to be considered further for potential use for treating neoplastic lesions.

5. Determining Whether A Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., *Cancer Research,* 55:3110–16, 1995, which is incorporated herein by reference). The novel features include collecting both floating and attached cells, identification of the optimal treatment times and dose range for observing apoptosis, and identification of optimal cell culture conditions.

Following treatment with a test compound, cultures can be assayed for apoptosis and necrosis by florescent microscopy following labeling with acridine orange and ethidium bromide. The method for measuring apoptotic cell number has previously been described by Duke & Cohen, "Morphological And Biochemical Assays Of Apoptosis," *Current Protocols In Immunology,* Coligan et al., eds., 3.17.1–3.17.16 (1992, which is incorporated herein by reference).

For example, floating and attached cells can be collected by trypsinization and washed three times in PBS. Aliquots of cells can be centrifuged. The pellet can then be resuspended in media and a dye mixture containing acridine orange and ethidium bromide prepared in PBS and mixed gently. The mixture can then be placed on a microscope slide and examined for morphological features of apoptosis.

Apoptosis can also be quantified by measuring an increase in DNA fragmentation in cells which have been treated with test compounds. Commercial photometric EIA for the quantitative in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e. cytoplasmic fraction) are transferred into a streptavidin-coated MTP. Care is taken not to shake the lysed pellets (i.e. cell nucleii containing high molecular weight, unfragmented DNA) in the MTP. Samples are then analyzed.

Fold stimulation (FS=$OD_{max}/OD_{veh}$), an indicator of apoptotic response, is determined for each compound tested at a given concentration. $EC_{50}$ values may also be determined by evaluating a series of concentrations of the test compound.

Statistically significant increases of apoptosis (i.e., greater than 2 fold stimulation at a concentration of 100 $\mu$M) are further indicative that the compound is useful for treating neoplastic lesions. Preferably, the $EC_{50}$ value for apoptotic activity should be less than 100 $\mu$M for the compound to be further considered for potential use for treating neoplastic lesions. $EC_{50}$ is herein defined as the concentration that causes 50% induction of apoptosis relative to vehicle treatment.

6. Mammary Gland Organ Culture Model Tests

Test compounds identified by the above methods can be tested for antineoplastic activity by their ability to inhibit the incidence of preneoplastic lesions in a mammary gland organ culture system. This mouse mammary gland organ culture technique has been successfully used by other investigators to study the effects of known antineoplastic agents such as NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed and thoracic mammary glands are excised aseptically and incubated for ten days in growth media supplemented with insulin, prolactin, hydrocortisone, and aldosterone. DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the premalignant lesions.

The test compound is dissolved in DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

7. Results of PDE, COX and In Vitro Neoplasia Inhibition

A number of compounds were examined in the various protocols and screened for potential use in treating neoplasia. The results of these tests are reported below. The test compounds are hereinafter designated by a letter code that corresponds to the following:

A—rac-threo-(E)-1-(N,N'-diethylaminoethanethio)-1-(butan-1',4'-olido)-[3',4':1,2]-6-fluoro-2-methyl-3-(p-methylsulfonylbenzylidene)-indan;

B—(Z)-5-Fluoro-2-methyl-1-(3,4,5-trimethoxybenzylidene)-3-acetic acid;

C—(Z)-5-Fluoro-2-methyl-1-(p-chlorobenzylidene)-3-acetic acid;

D—rac-(E)-1-(butan-1',4'-olido)-[3',4':1,2]-6-fluoro-2-methyl-3-(p-methylsulfonylbenzylidene)-1S-indanyl-N-acetylcysteine;

E—(Z)-5-Fluoro-2-methyl-1-(3,4,5-trimethoxybenzylidene)-3-indenylacetamide, N-benzyl;

F—(Z)-5-Fluoro-2-methyl-1-(p-methylsulfonylbenzylidene)-3-indenylacetamide, N,N'-dicyclohexyl;

G—ribo-(E)-1-Triazolo-[2',3':1",3"]-1-(butan-1',4'-olido)-[3',4':1,2]-6-fluoro-2-methyl-3-(p-methylsulfonylbenzylidene)-indan; and H—rac-(E)-1-(butan-1',4'-olido)-[3',4':1,2]-6-fluoro-2-methyl-3-(p-methylsulfonylbenzylidene)-1S-indanyl-glutathione).

EXAMPLE 1
COX Inhibition Assay

Figure 4:
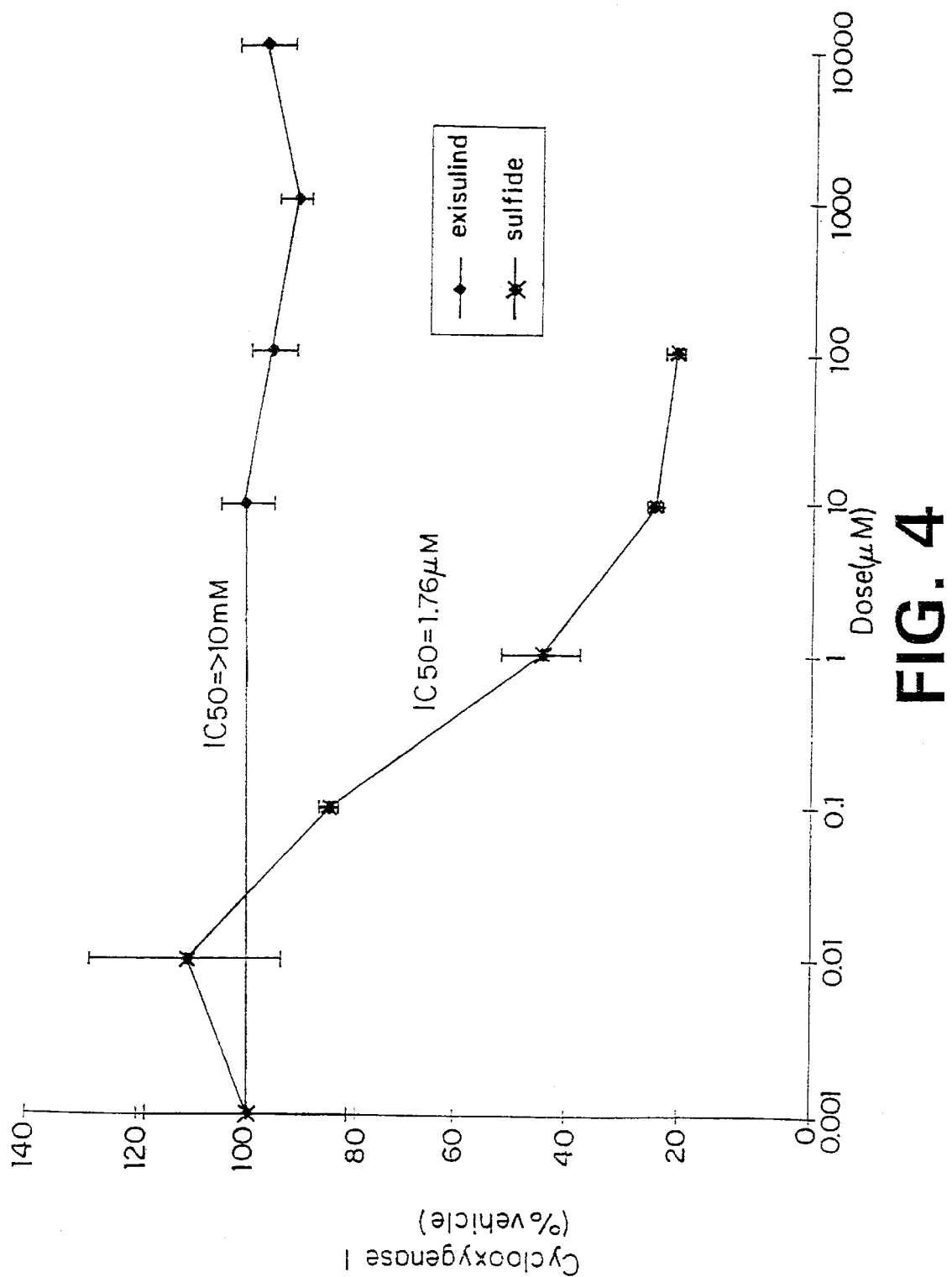
FIG. 4 illustrates the effect of the sulfide derivative of sulindac and the sulfone derivative of sulindac (a.k.a. exisulind) on purified cyclooxygenase activity.

Reference compounds and test compounds were analyzed for their COX inhibitory activity in accordance with the protocol for the COX assay, supra. FIG. 4 shows the effect of various concentrations of either sulindac sulfide or exisulind on purified cyclooxygenase (Type 1) activity. Cyclooxygenase activity was determined using purified cyclooxygenase from ram seminal vesicles as described previously (Mitchell et al, supra). The $IC_{50}$ value for sulindac sulfide was calculated to be approximately 1.76 $\mu$M, while that for exisulind was greater than 10,000 $\mu$M. These data show that sulindac sulfide, but not exisulind, is a COX-I inhibitor. Similar data were obtained for the COX-2 isoenzyme (Thompson, et al., Journal of the National Cancer Institute, 87: 1259–1260, 1995).

Figure 5:
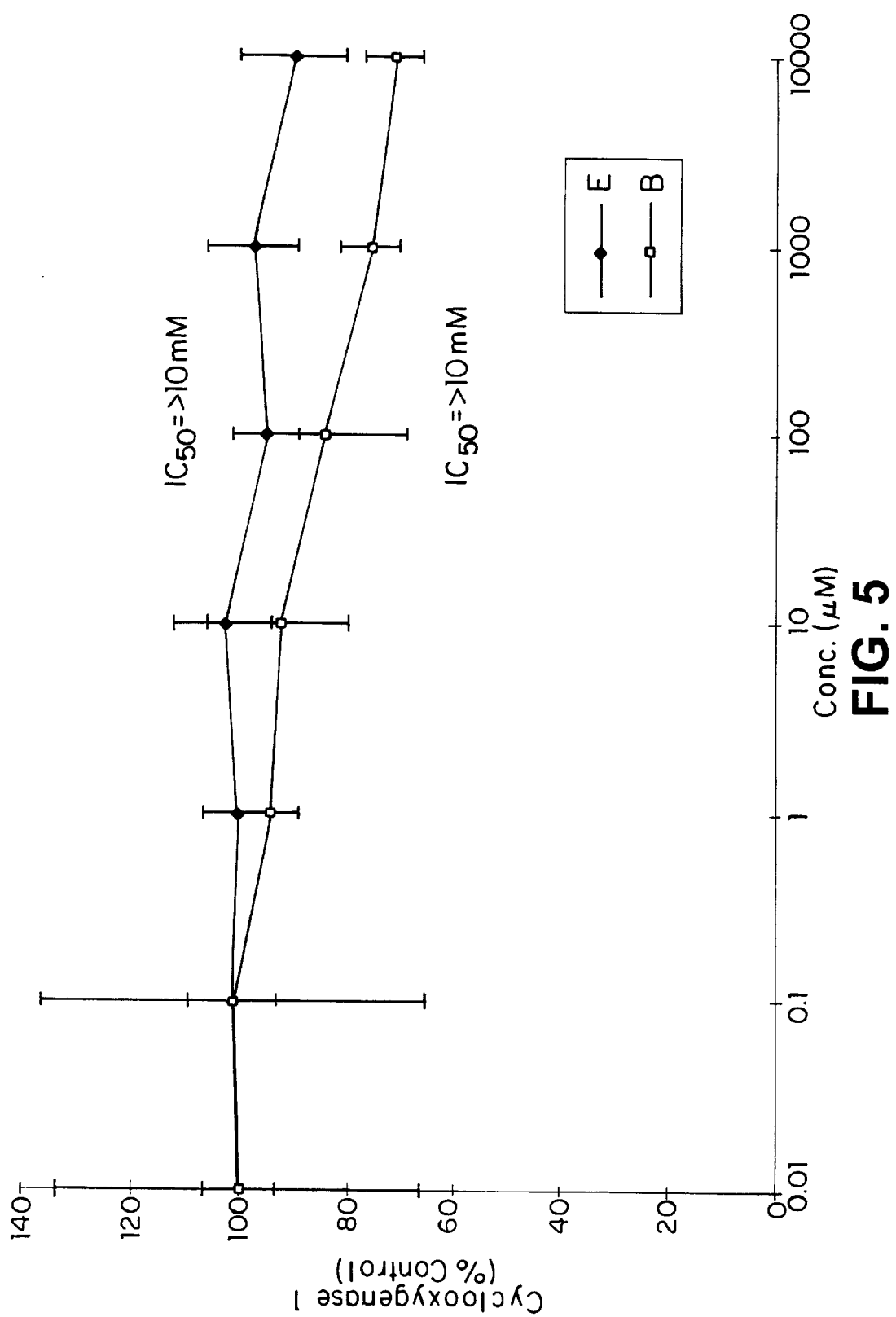
FIG. 5 illustrates the effects of test compounds B and E on COX inhibition.

FIG. 5 shows the effect of test compounds B and E on COX inhibition. COX activity was determined as for the compounds shown in FIG. 4. The data show that neither test compound B and E significantly inhibit COX-I.

TABLE 3

Cyclooxygenase inhibitory activity among a series of compounds

|  | % Inhibition at 100 $\mu$M |
| --- | --- |
| Reference compounds |  |
| Indomethacin | 95 |
| MY5445 | 94 |
| Sulindac sulfide | 97 |
| Exisulind | <25 |
| Test compounds |  |
| A | <25 |
| B | <25 |
| C | 87 |
| D | <25 |
| E | <25 |

In accordance with the protocol, supra, compounds A through E were evaluated for COX inhibitory activity as reported in Table 3 above. Compound C was found to inhibit COX greater than 25% at a 100 $\mu$M dose, and therefore, would not be selected for further screening.

EXAMPLE 2
cGMP PDE inhibition assay

Figure 6:
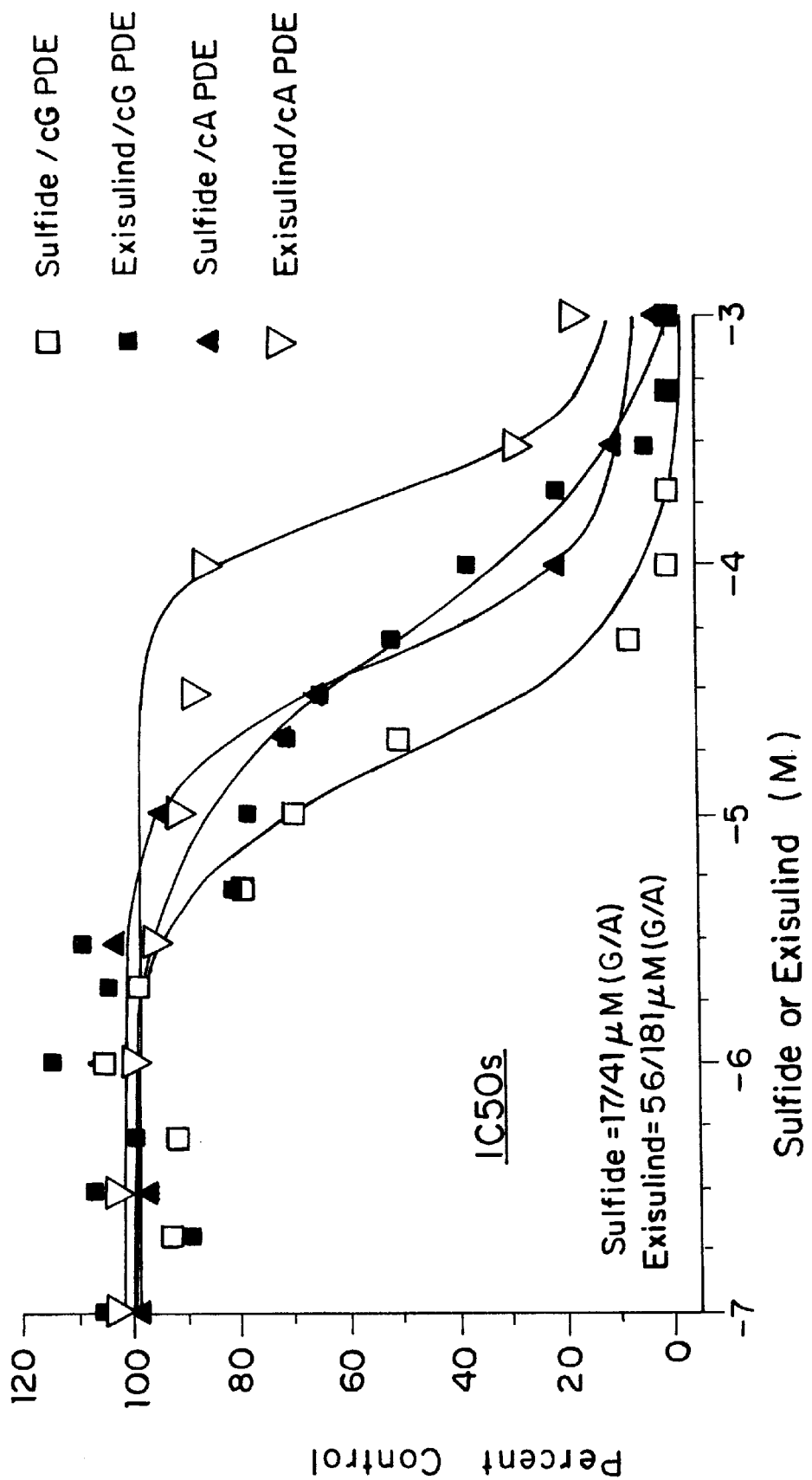
FIG. 6 illustrates the inhibitory effects of sulindac sulfide and exisulind on PDE4 and PDE5 purified from cultured tumor cells.

Reference compounds and test compounds were analyzed for their cGMP PDE inhibitory activity in accordance with the protocol for the assay described supra. FIG. 6 shows the effect of various concentrations of sulindac sulfide and exisulind on either PDE4 or cGMP PDE activity purified from human colon HT-29 cultured tumor cells, as described previously (W. J. Thompson et al., supra). The $IC_{50}$ value of sulindac sulfide for inhibition of PDE4 was 41 $\mu$M, and for inhibition of cGMP PDE was 17 $\mu$M. The $IC_{50}$ value of exisulind for inhibition of PDE4 was 181 $\mu$M, and for inhibition of cGMP PDE was 56 $\mu$M. These data show that both sulindac sulfide and exisulind inhibit phosphodiesterase activity. Both compounds show selectivity for the cGMP PDE isoenzyme forms over PDE4 isoforms.

Figure 7A:
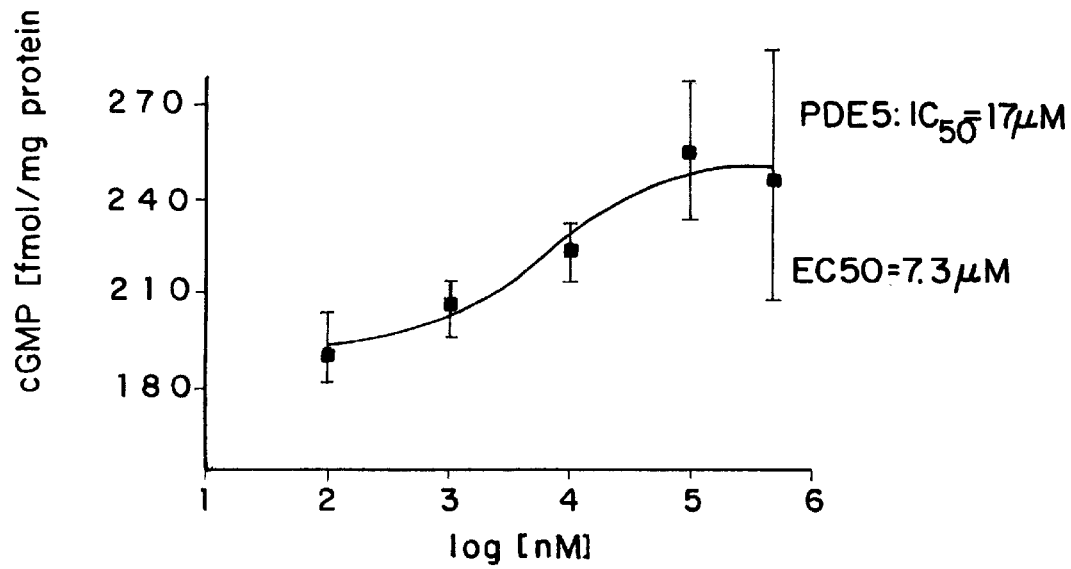
FIG. 7 illustrates the effects of sulindac sulfide on cyclic nucleotide levels in HT-29 cells.
Figure 7B:
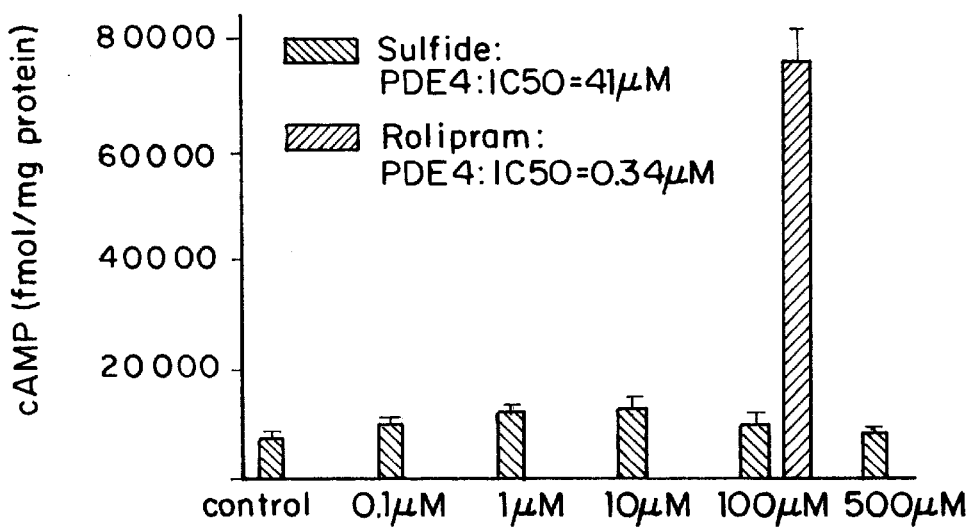

FIG. 7 shows the effects of sulindac sulfide on either cGMP or cAMP production as determined in cultured HT-29 cells in accordance with the assay described, supra. HT-29 cells were treated with sulindac sulfide for 30 minutes and cGMP or cAMP was measured by conventional radioimmunoassay method. As indicated, sulindac sulfide increased the levels of cGMP by greater than 50% with an $EC_{50}$ value of 7.3 $\mu$M (7A top). Levels of cAMP were unaffected by treatment, although a known PDE4 inhibitor, rolipram, increased cAMP (7B bottom). The data demonstrate the pharmacological significance of inhibiting cGMP PDE, relative to PDE4.

Figure 8:
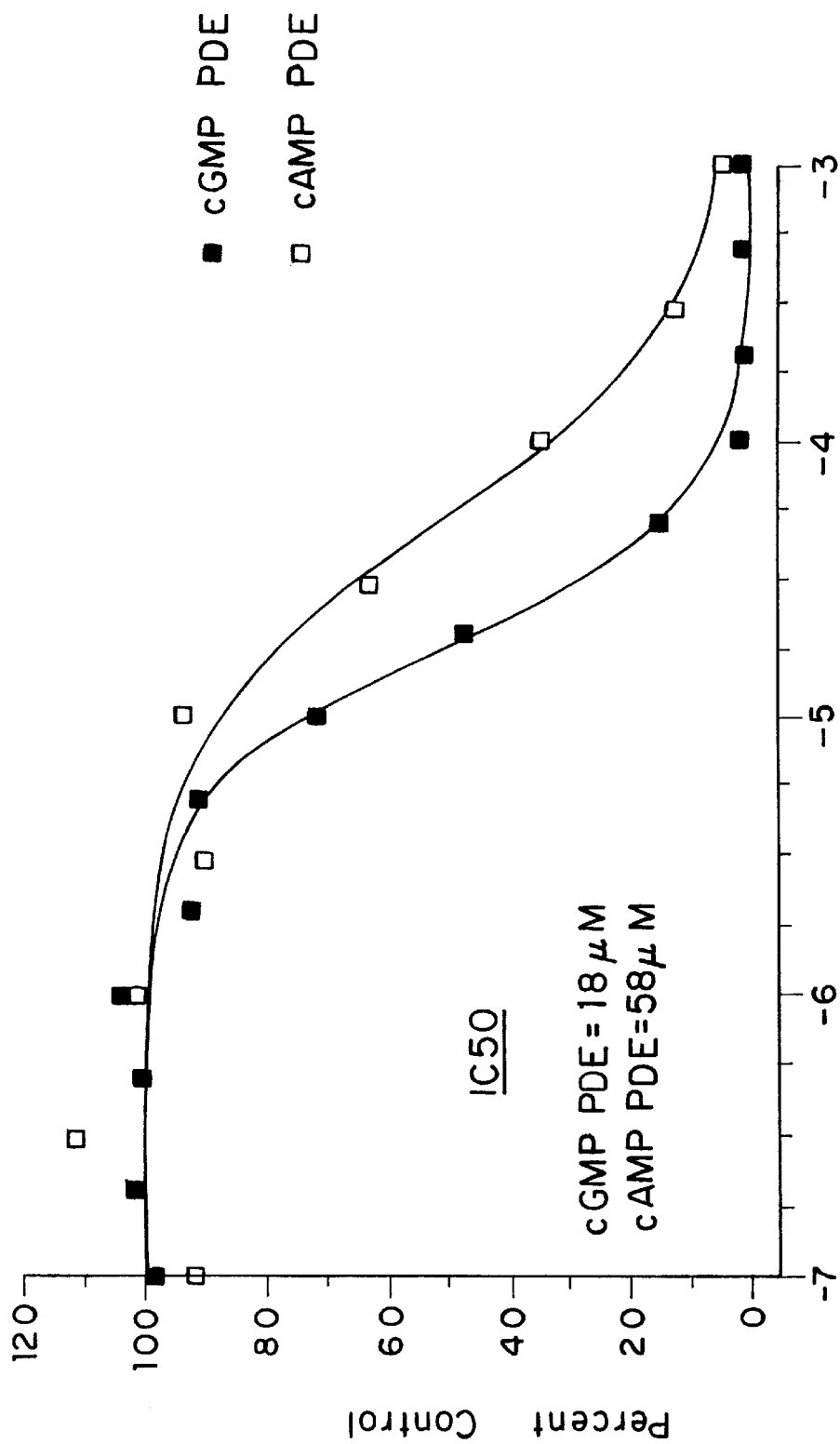
FIG. 8 illustrates the phosphodiesterase inhibitory activity of compound B.

FIG. 8 shows the effect of the indicated dose of test compound B on either cGMP PDE or PDE4 isozymes of phosphodiesterase. The calculated $IC_{50}$ value was 18 $\mu$M for cGMP PDE and was 58 $\mu$M for PDE4.

Figure 9:
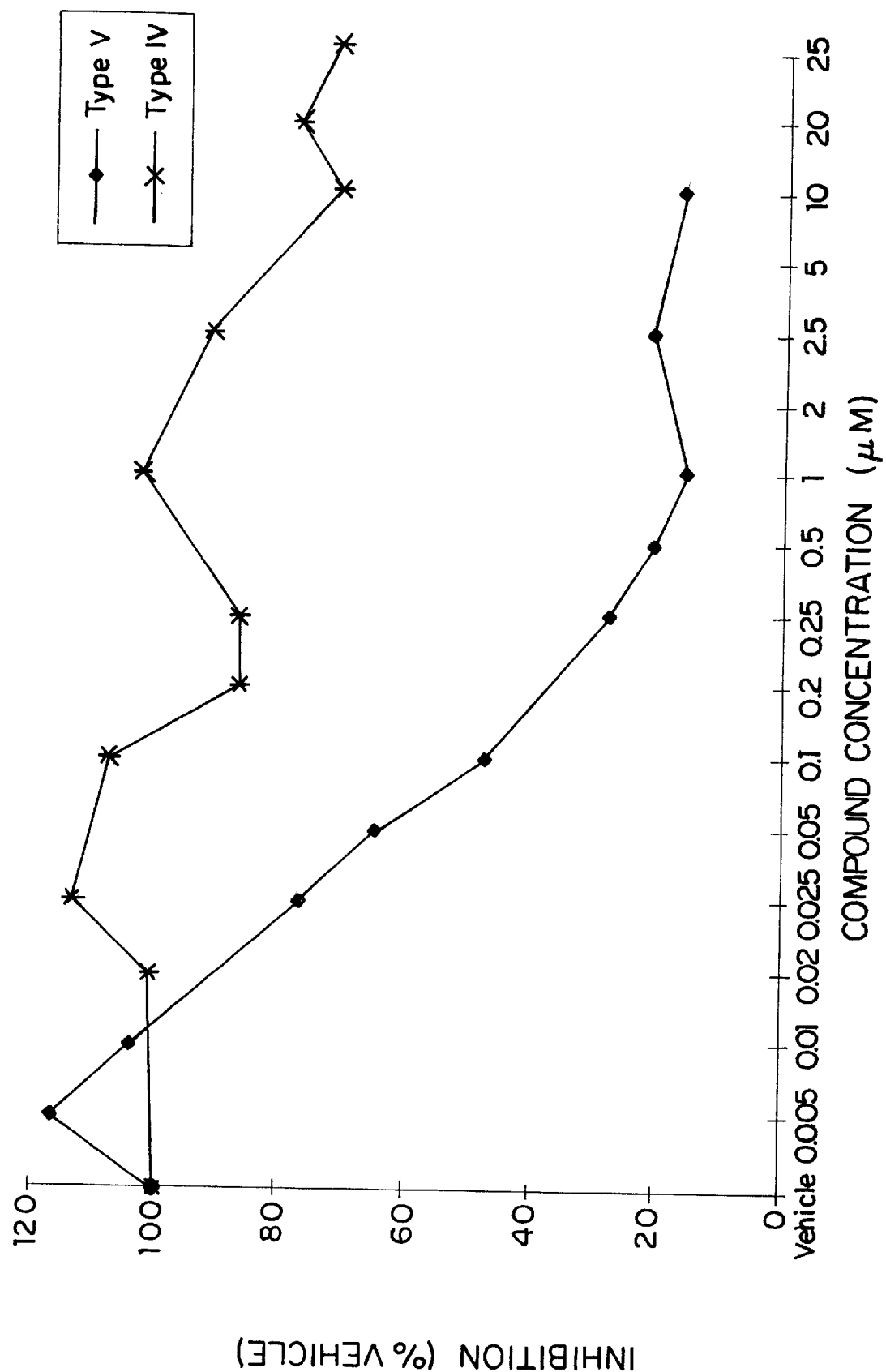
FIG. 9 illustrates the phosphodiesterase inhibitory activity of compound B.

FIG. 9 shows the effect of the indicated dose of test compound E on either PDE4 or cGMP PDE. The calculated $IC_{50}$ value was 0.08 $\mu$M for cGMP PDE and greater than 25 $\mu$M for PDE4.

TABLE 4 cGMP PDE inhibitory activity among a series of compounds

|  | % Inhibition at 10 $\mu$M |
| --- | --- |
| Reference compounds |  |
| Indomethacin | 34 |
| MY5445 | 86 |
| Sulindac sulfide | 97 |
| Exisulind | 39 |
| Test compounds |  |
| A | <25 |
| B | <25 |
| C | <25 |
| D | 36 |
| E | 75 |

The above compounds in Table 4 were evaluated for PDE inhibitory activity, as described in the protocol supra. Of the compounds that did not inhibit COX, only compound E was found to cause greater than 50% inhibition at 10 $\mu$M. As noted in FIG. 8, compound B showed inhibition of greater than 50% at a dose of 20 $\mu$M. Therefore, depending on the dosage level used in a single dose test, some compounds may be screened out that otherwise may be active at slightly higher dosages. The dosage used is subjective and may be lowered after active compounds are found at certain levels to identify even more potent compounds.

EXAMPLE 3
Apoptosis assay

Figure 10A:
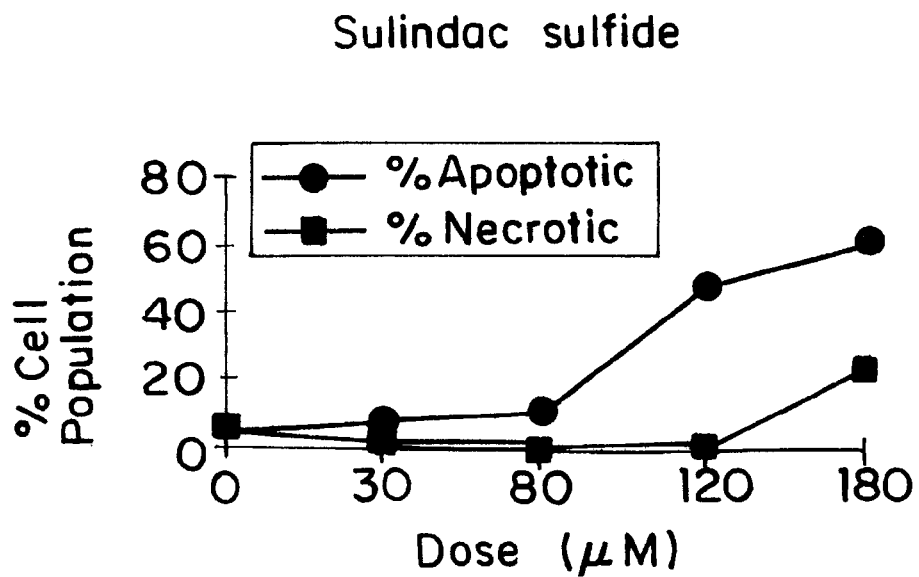
FIG. 10 illustrates the effects of sulindac sulfide and exisulind on apoptosis and necrosis of HT-29 cells.
Figure 10B:
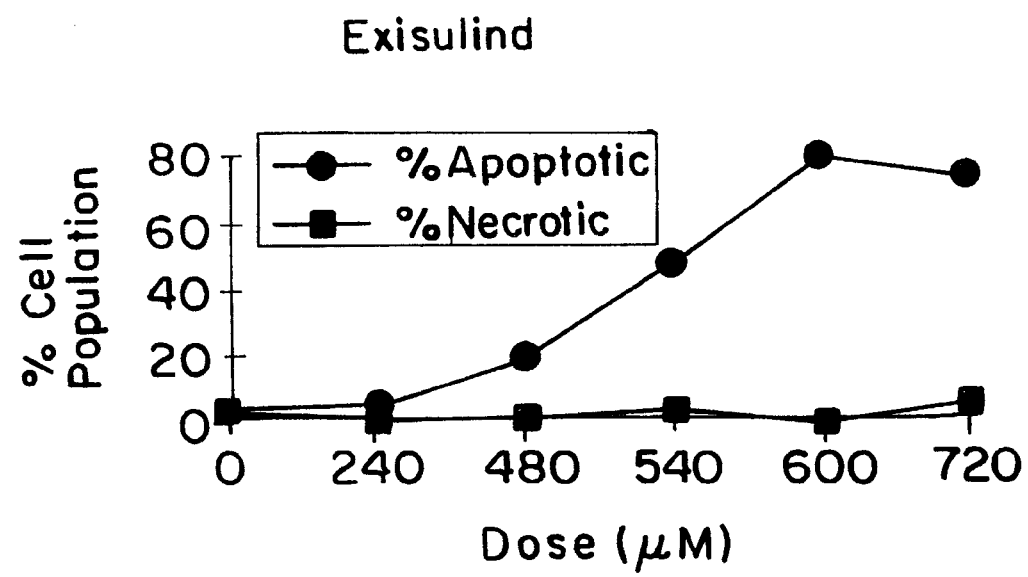

Reference compounds and test compounds were analyzed for their novel PDE inhibitory activity in accordance with the protocols for the assay, supra. In accordance with thos protocols, FIG. 10 shows the effects of sulindac sulfide and exisulind on apoptotic and necrotic cell death. HT-29 cells were treated for six days with the indicated dose of either sulindac sulfide or exisulind. Apoptotic and necrotic cell death was determined previously (Duke and Cohen, In: Current Protocols in Immunology, 3.17.1–3.17.16, New York, John Wiley and Sons, 1992). The data show that both sulindac sulfide and exisulind are capable of causing apoptotic cell death without inducing necrosis. All data were collected from the same experiment.

Figure 11A:
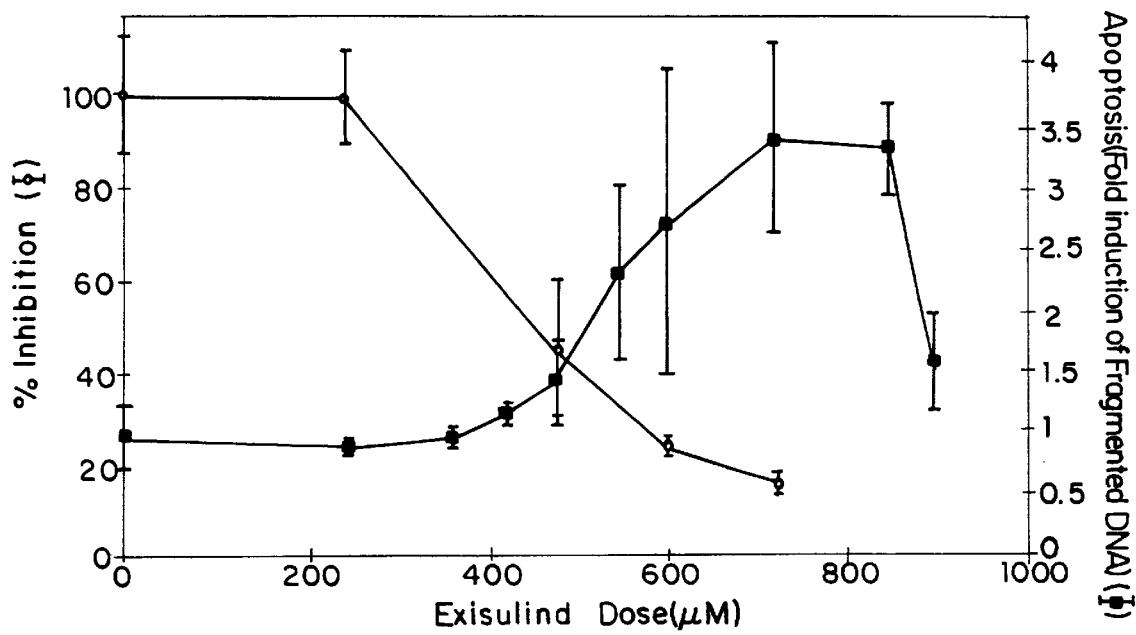
FIG. 11 illustrates the effects of sulindac sulfide and exisulind on HT-29 cell growth inhibition and apoptosis induction as determined by DNA fragmentation.
Figure 11B:
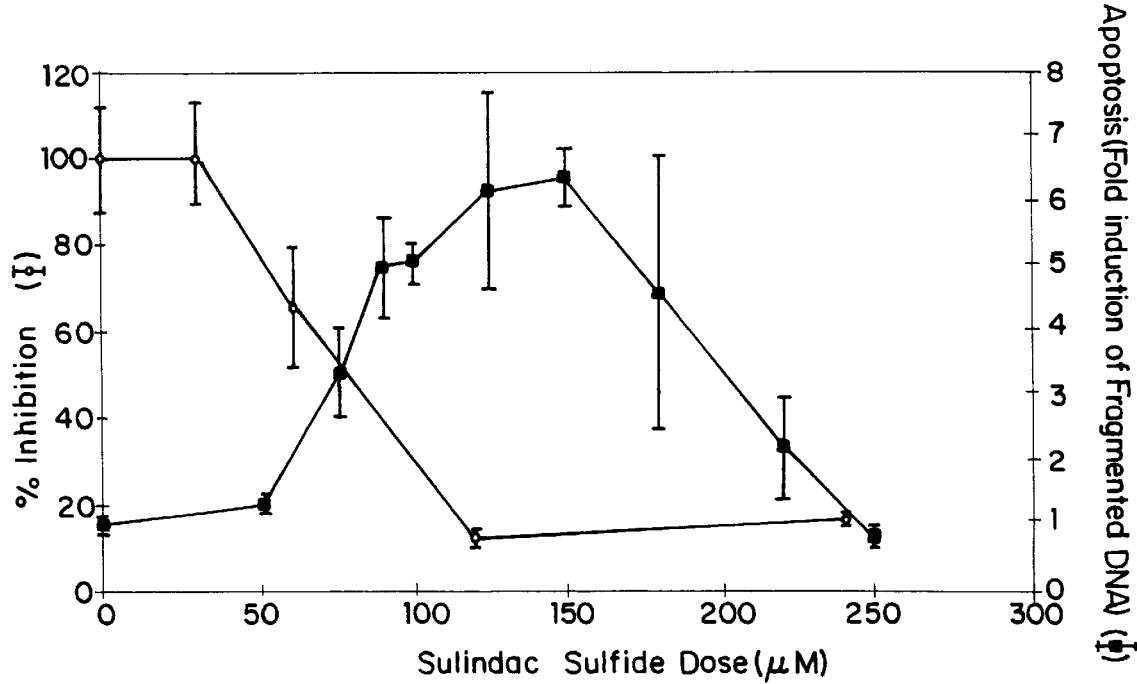

FIG. 11 shows the effect of sulindac sulfide and exisulind on tumor growth inhibition and apoptosis induction as determined by DNA fragmentation. Top FIG. (11A); growth inhibition (open symbols, left axis) and DNA fragmentation (closed symbols, right axis) by exisulind. Bottom FIG. (11B); growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment.

Figure 12:
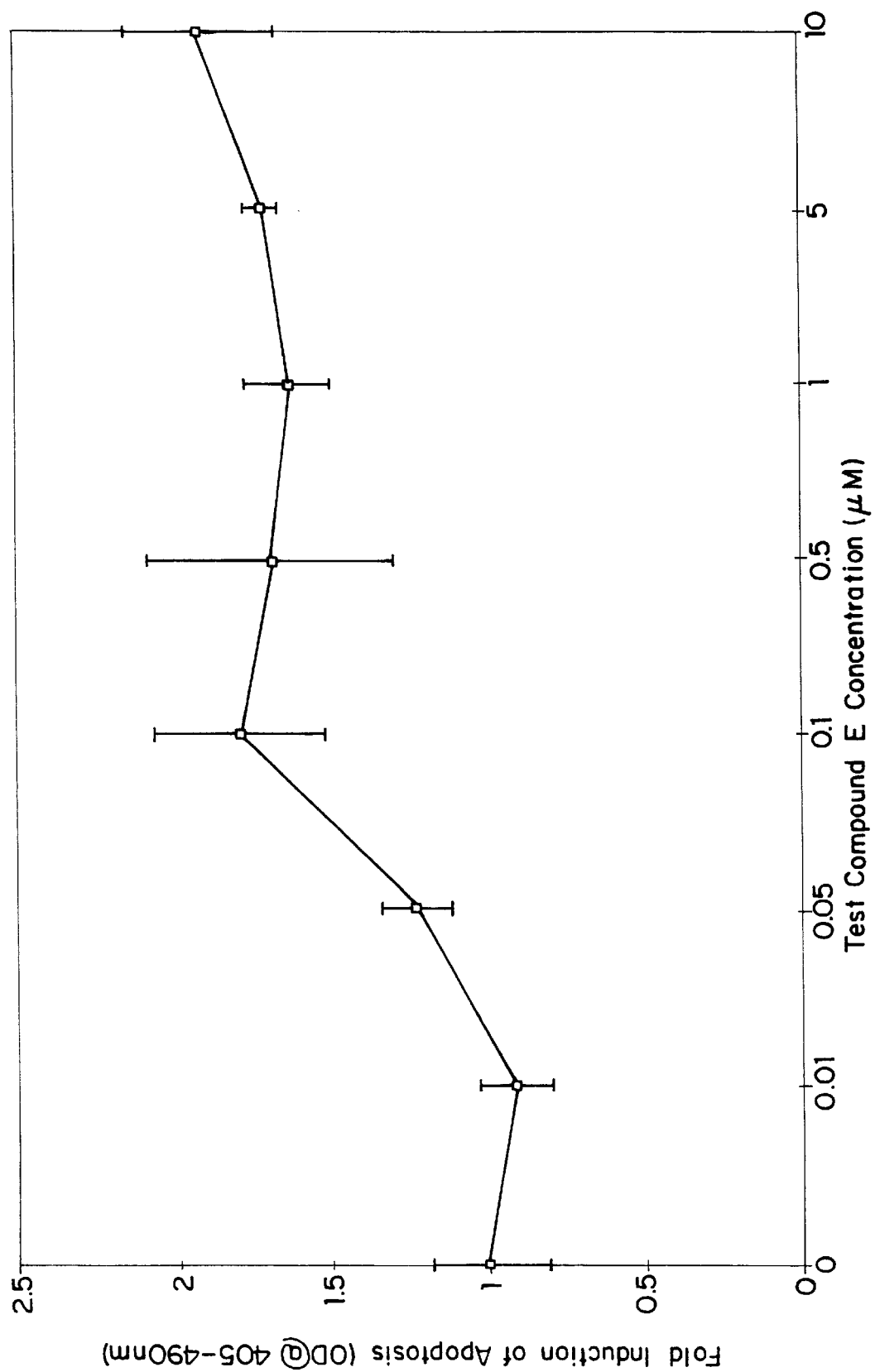
FIG. 12 illustrates the apoptosis inducing properties of compound E.

FIG. 12 shows the apoptosis inducing properties of compound E. HT-29 colon adenocarcinoma cells were treated with the indicated concentration of compound E for 48 hours and apoptosis was determined by the DNA fragmentation assay. The calculated $EC_{50}$ value was 0.05 μM.

Figure 13:
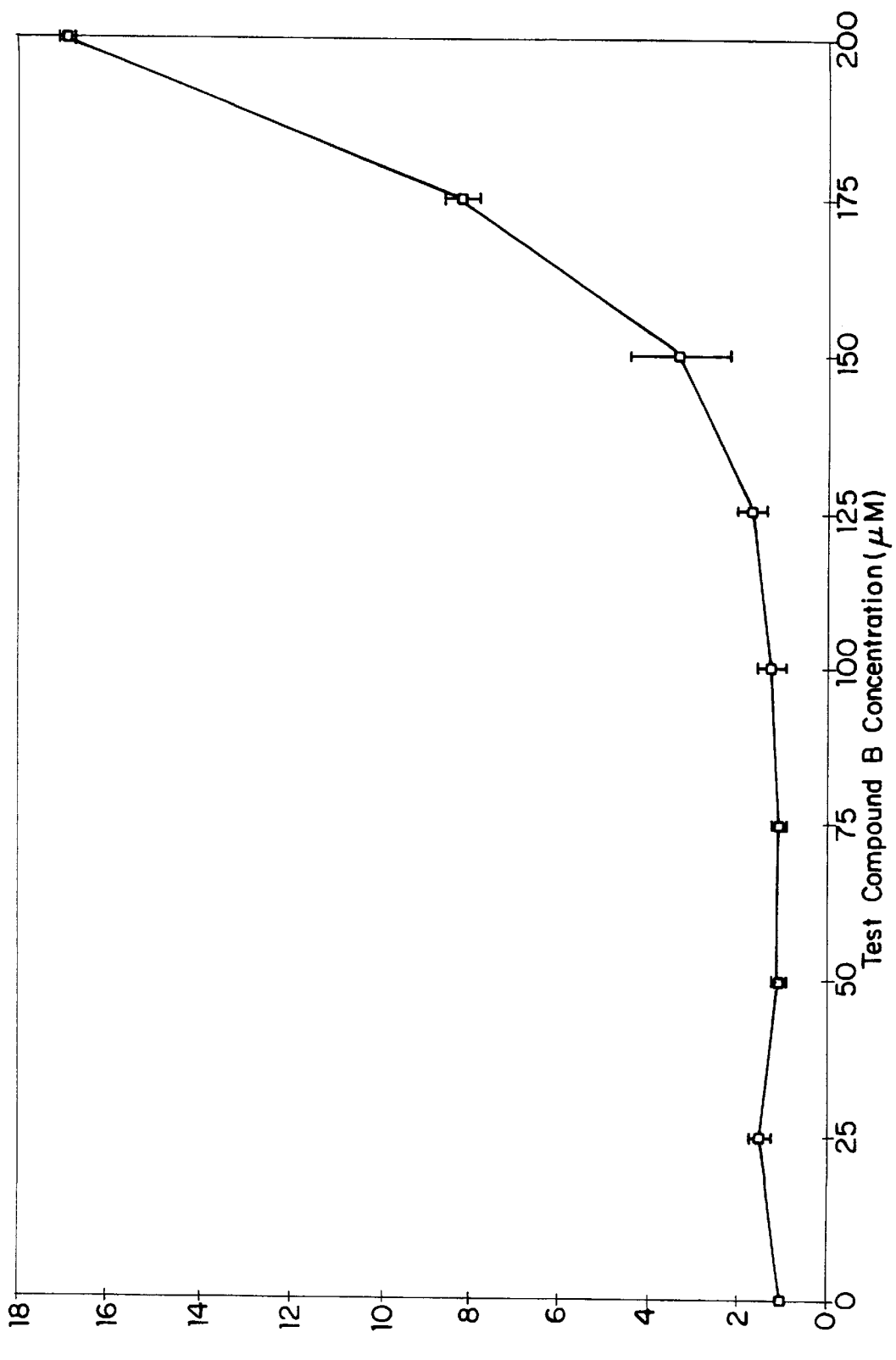
FIG. 13 illustrates the apoptosis inducing properties of compound B.

FIG. 13 shows the apoptosis inducing properties of compound B. HT-29 colon adenocarcinoma cells were treated with the indicated concentration of compound B for 48 hours and apoptosis was determined by the DNA fragmentation assay. The calculated $EC_{50}$ value was approximately 175 μM.

TABLE 5

Apoptosis inducing activity among a series of compounds

|  | Fold induction at 100 μM |
|---|---|
| Reference compounds |  |
| Indomethacin | <2.0 |
| MY5445 | 4.7 |
| Sulindac sulfide | 7.9 |
| Exisulind | <2.0 |
| E4021 | <2.0 |
| Zaprinast | <2.0 |
| Sildenafil | <2.0 |
| EHNA | <2.0 |
| Test compounds |  |
| A | <2.0 |
| B | 3.4 |
| C | 5.6 |
| D | <2.0 |
| E | 4.6 |

In accordance with the fold induction protocol, supra, the compounds A through E were tested for apoptosis inducing activity, as reported in Table 5 above. Compounds B, C and E showed significant apoptotic inducing activity, greater than 2.0 fold, at a dosage of 100 μM. Of these three compounds, at this dosage only B and E did not inhibit COX but did inhibit cGMP-specific PDE.

The apoptosis inducing activity for a series of phosphodiesterase inhibitors was determined. The data are shown in Table 6 below. HT-29 cell were treated for 6 days with various inhibitors of phosphodiesterase. Apoptosis and necrosis were determined morphologically after acridine orange and ethidium bromide labeling in accordance with the assay described, supra. The data show that the novel cGMP-specific PDE is useful for screening compounds that induce apoptosis of HT-29 cells.

TABLE 6

Apoptosis-Induction Data for PDE Inhibitors

| Inhibitor | Reported Selectivity | % Apoptosis | % Necrosis |
|---|---|---|---|
| Vehicle |  | 8 | 6 |
| 8-methoxy-IBMX | PDE1 | 2 | 1 |
| Milrinone | PDE3 | 18 | 0 |

TABLE 6-continued

Apoptosis-Induction Data for PDE Inhibitors

| Inhibitor | Reported Selectivity | % Apoptosis | % Necrosis |
|---|---|---|---|
| RO-20-1724 | PDE4 | 11 | 2 |
| MY5445 | PDE5 | 80 | 5 |
| IBMX | Non-selective | 4 | 13 |

EXAMPLE 4

Growth inhibition assay

Figure 14:
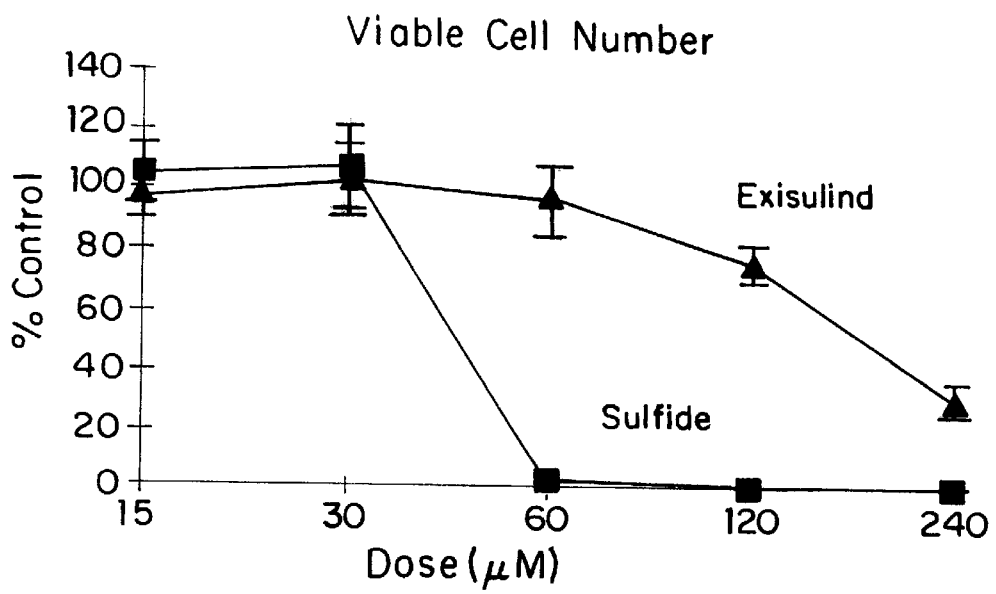
FIG. 14 illustrates the effects of sulindac sulfide and exisulind on tumor cell growth.

Reference compounds and test compounds were analyzed for their PDE5 inhibitory activity in accordance with the protocol for the assay supra. FIG. 14 shows the inhibitory effect of various concentrations of sulindac sulfide and exisulind on the growth of HT-29 cells. HT-29 cells were treated for six days with various doses of exisulind (triangles) or sulindac sulfide (squares) as indicated. Cell number was measured by a sulforhodamine assay as previously described (Piazza et al., Cancer Research, 55: 3110–3116, 1995). The $IC_{50}$ value for sulindac sulfide was approximately 45 μM and 200 μM for the exisulind. The data show that both sulindac sulfide and exisulind are capable of inhibiting tumor cell growth.

Figure 15A:
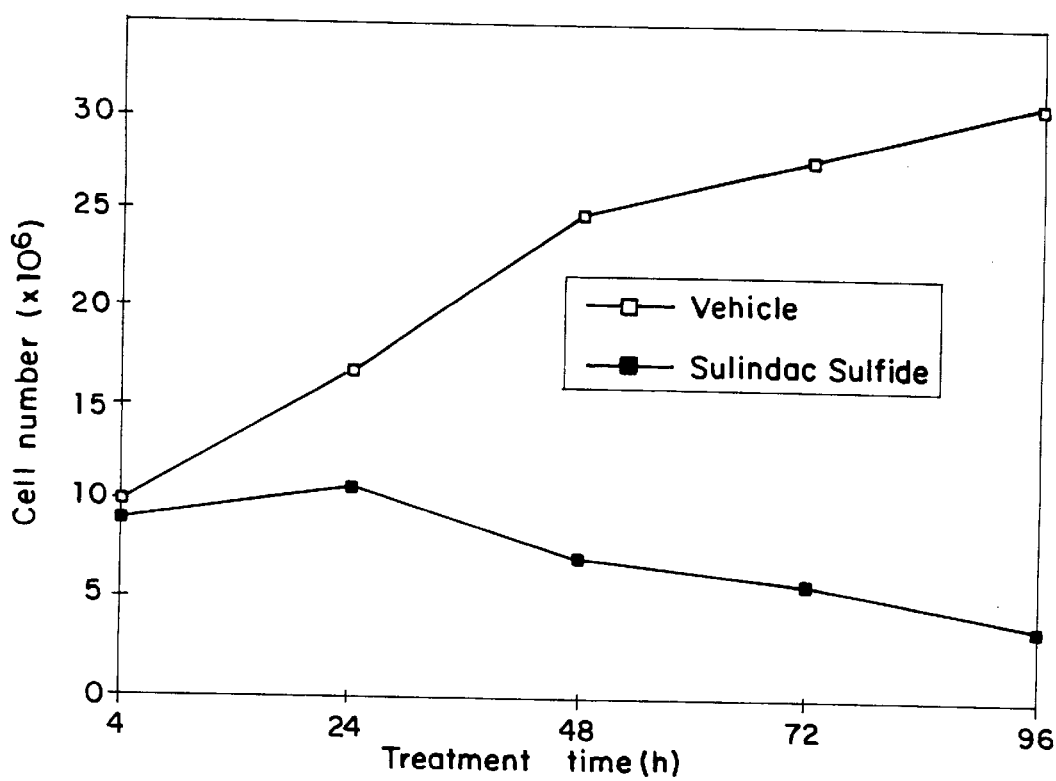
FIG. 15 illustrates the growth inhibitory and apoptosis-inducing activity of sulindac sulfide and control (DMSO).
Figure 15B:
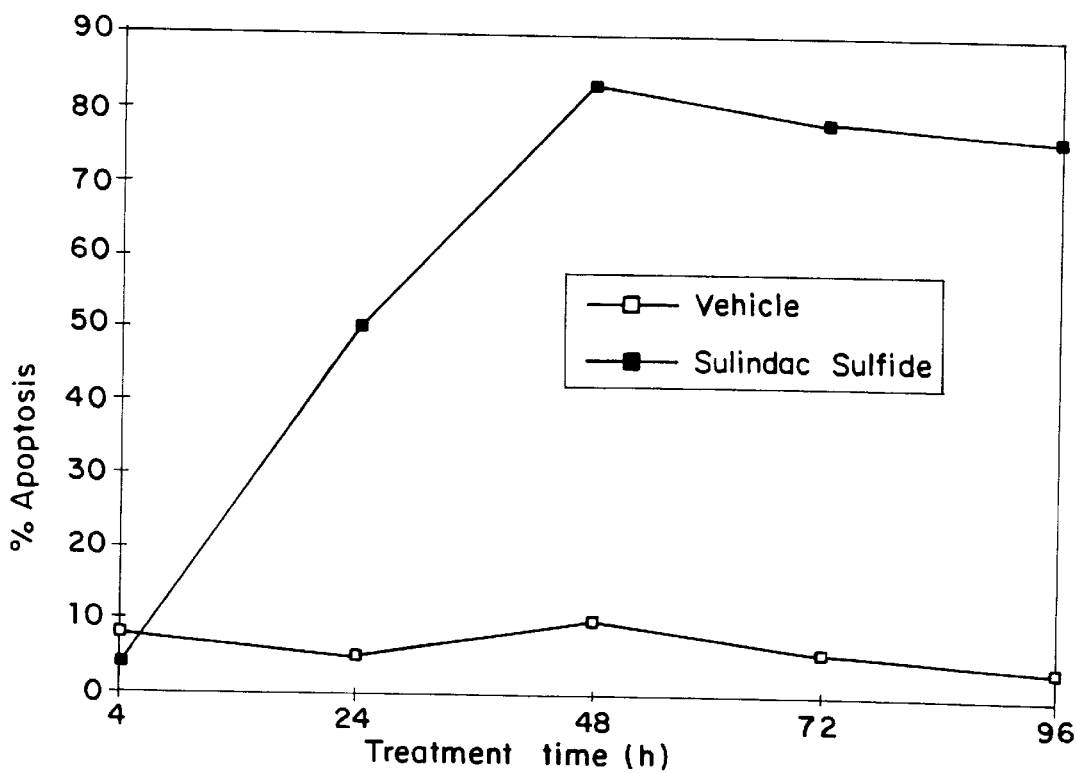

FIG. 15 shows the growth inhibitory and apoptosis-inducing activity of sulindac sulfide. A time course experiment is shown involving HT-29 cells treated with either vehicle, 0.1% DMSO (open symbols) or sulindac sulfide, 120 μM (closed symbols). Growth inhibition (15A top) was measured by counting viable cells after trypan blue staining. Apoptosis (15B bottom) was measured by morphological determination following staining with acridine orange and ethidium bromide as described previously (Duke and Cohen, In: Current Protocols in Immunology, 3.17.1–3.17.16, New York, John Wiley and Sons, 1992). The data demonstrate that sulindac sulfide is capable of inhibiting tumor cell growth and that the effect is accompanied by an increase in apoptosis. All data were collected from the same experiment.

FIG. 16 shows the growth inhibitory activity of test compound E. HT-29 colon adenocarcinoma cells were treated with the indicated concentration of compound E for six days and cell number was determined by the SRB assay. The calculated $IC_{50}$ value was 0.04 μM.

TABLE 7

Growth inhibitory activity among a series of compounds

|  | % Inhibition at 100 μM |
|---|---|
| Reference compounds |  |
| Indomethacin | 75 |
| MY5445 | 88 |
| Sulindac sulfide | 88 |
| Exisulind | <50 |
| E4021 | <50 |
| sildenafil | <50 |
| zaprinast | <50 |
| Test compounds |  |
| A | 68 |
| B | 77 |
| C | 80 |
| D | 78 |
| E | 62 |

In accordance with the screening protocol of section supra, compounds A through E were tested for growth inhibitory activity, as reported in Table 7 above. All the test compounds showed activity.

The growth inhibitory activity for a series of phosphodiesterase inhibitors was determined. The data are shown in Table 8 below. HT-29 cell were treated for 6 days with various inhibitors of phospohodiesterase. Cell growth was determined by the SRB assay described, supra. The data below taken with those above show that inhibitors of the novel PDE were effective for inhibiting tumor cell growth.

TABLE 8

Growth Inhibitory Data for PDE Inhibitors

| Inhibitor | Reported Selectivity | Growth inhibition ($IC_{50}$, $\mu M$) |
|---|---|---|
| 8-methoxy-IBMX | PDE1 | >200 $\mu M$ |
| Milrinone | PDE3 | >200 $\mu M$ |
| RO-20-1724 | PDE4 | >200 $\mu M$ |
| MY5445 | PDE5 | 5 $\mu M$ |
| IBMX | Non-selective | >100 $\mu M$ |
| Zaprinast | PDE5 | >100 $\mu M$ |
| Sildenafil | PDE5 | >100 $\mu M$ |
| E4021 | PDE5 | >100 $\mu M$ |

To show the effectiveness of this screening method on various forms of neoplasia, compounds were tested on numerous cell lines. The effects of sulindac sulfide and exisulind on various cell lines were determined. The data are shown in table 9 below. The $IC_{50}$ values were determined by the SRB assay. The data show the broad effectiveness of these compounds on a broad range of neoplasias, with effectiveness at comparable dose range. Therefore, compounds identified by this invention should be useful for treating multiple forms of neoplasia.

TABLE 9

Growth Inhibitory Data of Various Cell Lines

| Cell Type/ Tissue specificity | $IC_{50}$ ($\mu M$) | | |
|---|---|---|---|
| | Sulindac sulfide | Ex- isulind | Compound E* |
| HT-29, Colon | 60 | 120 | 0.10 |
| HCT116, Colon | 45 | 90 | |
| MCF7/S, Breast | 30 | 90 | |
| UACC375, Melanoma | 50 | 100 | |
| A-427, Lung | 90 | 130 | |
| Bronchial Epithelial Cells | 30 | 90 | |
| NRK, Kidney (non ras-transformed) | 50 | 180 | |
| KNRK, Kidney (ras transformed) | 60 | 240 | |
| Human Prostate Carcinoma PC3 | | 82 | 0.90 |
| Colo 205 | | | 1.62 |
| DU-145 | | | 0.10 |
| HCT-15 | | | 0.60 |
| MDA-MB-231 | | | 0.08 |
| MDA-MB-435 | | | 0.04 |

*Determined by neutral red assay as described by Schmid et al., in Proc. AACR Vol 39, p. 195 (1998).

EXAMPLE 5
Activity in mammary gland organ culture model

Figure 17:
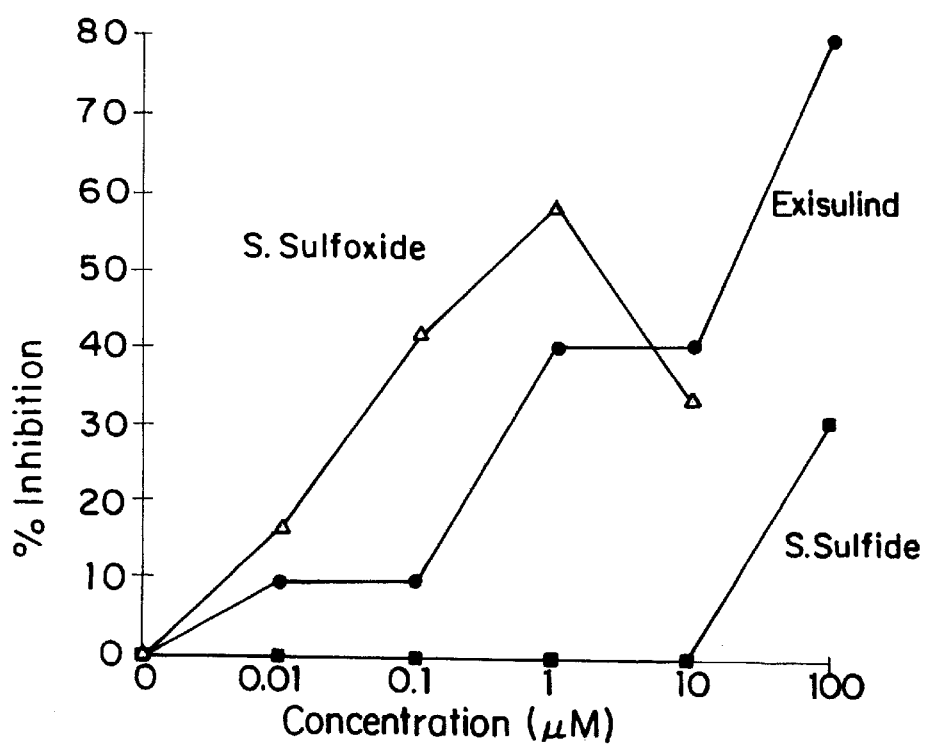
FIG. 17 illustrates the inhibition of pre-malignant, neoplastic lesions in mouse mammary gland organ culture by sulindac metabolites.

FIG. 17 shows the inhibition of premalignant lesions in mammary gland organ culture by sulindac metabolites. Mammary gland organ culture experiment were performed as previously described (Mehta and Moon, Cancer Research, 46: 5832–5835, 1986). The results demonstrate that sulindac and exisulind effectively inhibit the formation of premalignant lesions, while sulindac sulfide was inactive. The data support the hypothesis that cyclooxygenase inhibition is not necessary for the anti-neoplastic properties of desired compounds.

These results indicate that a compound that causes PKG activity to increase also can induce apoptosis and inhibit growth in neoplastic cells.

EXAMPLE 6
Selecting a Compound for Human Clinical Use

As indicated above, a number of neoplasias harbor the APC mutation. Among other things, the verification of the selection process of this invention was established in human clinical trials in patients with neoplasia harboring the APC mutation.

The APC mutation was first discovered in patients with the hereditary neoplasia, adenomatous polyposis coli ("APC"). The APC disease is characterized by the appearance in the teen years of hundreds to thousands of polyps in the colon, and the common therapy is surgical removal of the colon before the age of 20.

A human clinical study was performed in APC patients, selecting exisulind in each instance. In that study, each patient had already had his/her colon removed, except for a small section of colon adjacent the rectum (where the small intestine was attached) to preserve rectal function. However, such a patient commonly forms polyps in the small remaining colonic section, which polyps require periodic removal (e.g., by electrocautery).

That trial where exisulind was selected was a prevention trial designed to compare the cumulative number of new polyps formed over twelve months by the drug and placebo groups. Eligible patients were those who form between 9 and 44 polyps per year. Patients were fully ablated (had all polyps removed) at the start of the study, at the end of 6 months and at the end of 12 months. The study enrolled thirty-four eligible patients. Based on the estimated mean number of polyps formed over a year in APC patients who had historically produced 9 to 44 polyps per year, exisulind was clinically and statistically significantly better than placebo in decreasing the rate of polyp formation. Based on the median number of polyps produced in the first six months of the study, patients treated with exisulind developed approximately one-third the number of polyps as patients treated with placebo (median values 9 polyps/year and 26 polyps/year, respectively; p=0.013). Based on the median number of polyps produced over the entire 12 months of the study, patients treated with exisulind produced approximately half the number of polyps as patients treated with placebo (median values 18 polyps/year and 38 polyps/year, respectively; p=0.020).

A separate clinical trial was also performed on male patients who had prostate cancer, and as a result had their prostates removed. The study was conducted in patients with detectable PSA (prostate specific antigen) levels that were rising following radical prostatectomy, indicating recurrence of prostate cancer.

96 patients were enrolled in the prostate study: a double-blind, placebo-controlled, multi-center trial involving exisulind administered to the drug-receiving patients at 500 mg/day. As presented below, the data showed a statistically significant difference in PSA levels between the exisulind-treated group and the placebo-treated group. PSA levels in the exisulind-treated group were significantly reduced as compared with the PSA levels of the placebo-treated group. Although a rising level of PSA is not itself a disease condition, it is widely regarded in the medical community as a surrogate marker indicative of the presence of recurrence of prostate cancer in such men.

In addition to performing an analysis based on the differences in mean PSA levels between the exisulind and placebo groups as a whole, the interim analysis included subgroup analysis. The patients in the study were classified into high, intermediate and low risk groups in terms of their risk of developing metastatic disease. This classification was performed by a researcher at Johns Hopkins University, using the methodology published by him and other Johns Hopkins' researchers in the *Journal of the American Medical Association* (JAMA May 5, 1999, pp. 1591–97). To ascertain which study patients fell into which risk group, medical histories were supplied to the researcher who was blinded as to whether patients were on drug or placebo; he assigned study patients to the appropriate risk groups according to the above referenced published methodology. The statistical analysis revealed statistically significant differences in mean PSA levels between exisulind and placebo patients in both high and intermediate risk groups.

The data from the prostate study are as follows:

TABLE 1

Effect of Exisulind On Mean PSA Level
In Men Post-Prostatectomy With Rising PSA

| Group | Placebo | Exisulind | "p" value |
|---|---|---|---|
| Overall | 4.49 | 2.85 | 0.0004 |
| High Risk | 4.98 | 2.91 | 0.0002 |
| Intermediate Risk | 6.24 | 2.95 | 0.0053 |

These results illustrate that selecting a compound that causes PKG activity to increase (as well as meeting the other selection criteria of this invention) can result in a therapeutically effective drug, in vivo.

Obviously, numerous modifications and variations of the present invention are possible in light of the above teachings. It is therefore to be understood that within the scope of the appended claims, the invention may be practiced otherwise than as specifically described herein.

We claim:

1. A method of selecting a compound for treatment of a neoplasia, comprising:
    (a) evaluating the anti-neoplastic activity of the compound against said neoplasia;
    (b) evaluating whether the compound increases protein kinase G activity in said neoplasia; and
    (c) selecting the compound that exhibits anti-neoplastic activity and that induces an increase protein kinase G activity in said neoplasia.

2. The method of claim 1 further comprising evaluating whether the compound inhibits PDE5, and selecting the compound that inhibits PDE5.

3. The method of claim 1 further comprising evaluating whether the compound reduces β-catenin in neoplasia, and selecting the compound that so reduces β-catenin.

4. The method of claim 1 further comprising evaluating whether the compound inhibits cGMP-specific phosphodiesterase ("PDE") and selecting the compound that inhibits said PDE.

5. The method of claim 1 further comprising evaluating whether the compound increases protein kinase G expression, and selecting the compound if it increases PKG expression.

6. The method of claim 1 further comprising evaluating whether the compound increases protein kinase G activation, and selecting the compound if it increases PKG activation.

7. A method of selecting a compound for treatment of a neoplasia, comprising:
    (a) evaluating whether the compound increases protein kinase G activity in a neoplasia;
    (b) evaluating whether the compound reduces β-catenin in said neoplasia; and
    (c) selecting the compound that causes an increase protein kinase G activity and causes a decrease in β-catenin for the treatment of neoplasia.

8. A method for identifying a compound with potential for treating neoplasia, comprising:
    selecting a compound that increases protein kinase G activity in the neoplasia; and
    evaluating the neoplasia growth inhibiting activity of the compound identifying a compound that increases protein kinase G activity and has neoplasia growth inhibiting activity as a compound to treat neoplasia.

9. A method for identifying a compound with potential for treating neoplasia, comprising
    determining the cyclooxygenase (COX) inhibitory activity of the compound; and
    determining whether the compound increases protein kinase G activity in neoplastic cells;
    wherein low COX inhibitory activity and an increase in protein kinase G activity identifies that the compound has potential for treating neoplasia.

10. The method of claim 9, further comprising
    determining whether the compound inhibits tumor cell growth in a sample;
    wherein inhibition of tumor cell growth is further indicative that the compound is useful for treating neoplasia.

11. A method of selecting a compound for treating neoplastic cells, comprising
    determining the neoplastic cell growth inhibitory activity of the compound;
    determining whether the compound increases protein kinase G activity in neoplastic cells; and
    selecting the compound that exhibits neoplastic cell growth inhibitory activity and an increase in protein kinase G activity in neoplastic cells.

12. A method for selecting a compound for treatment of a neoplasia, comprising contacting said compound to said neoplasia, evaluating whether protein kinase G causes β-catenin to be phosphorylated in said neoplasia exposed to said compound, and selecting the compound that causes protein kinase G to phosphorylate β-catenin as the compound for the treatment of said neoplasia.

* * * * *